US008308699B2

(12) United States Patent
Zhang et al.

(10) Patent No.: US 8,308,699 B2
(45) Date of Patent: Nov. 13, 2012

(54) LAYERED NON-FOULING, ANTIMICROBIAL ANTITHROMBOGENIC COATINGS

(75) Inventors: Zheng Zhang, Cambridge, MA (US); Chad Huval, Somerville, MA (US); William Shannan O'Shaughnessey, Boston, MA (US); Michael Hencke, Cambridge, MA (US); Trevor Squier, Peabody, MA (US); Jun Li, Brookline, MA (US); Michael Bouchard, Wyomissing, PA (US); Christopher R. Loose, Cambridge, MA (US)

(73) Assignee: Semprus Biosciences Corp., Cambridge, MA (US)

( * ) Notice: Subject to any disclaimer, the term of this patent is extended or adjusted under 35 U.S.C. 154(b) by 235 days.

(21) Appl. No.: 12/632,669

(22) Filed: Dec. 7, 2009

(65) Prior Publication Data

US 2010/0145286 A1  Jun. 10, 2010

Related U.S. Application Data

(60) Provisional application No. 61/120,285, filed on Dec. 5, 2008, provisional application No. 61/120,292, filed on Dec. 5, 2008, provisional application No. 61/120,302, filed on Dec. 5, 2008, provisional application No. 61/255,264, filed on Oct. 27, 2009.

(51) Int. Cl.
*A61M 25/00* (2006.01)
*C08F 290/14* (2006.01)
*C08F 112/08* (2006.01)
*C08F 283/04* (2006.01)
*C08F 120/10* (2006.01)
*C08F 20/56* (2006.01)
*C08F 283/02* (2006.01)
*C08G 77/38* (2006.01)

(52) U.S. Cl. ............ 604/265; 428/413; 428/474.4; 428/480; 442/123; 525/329.1; 525/329.4; 525/330.3; 525/333.3; 525/333.7; 525/418; 525/419; 525/453; 525/462; 525/474; 525/50; 525/523; 525/535; 536/123.1

(58) Field of Classification Search ............ None
See application file for complete search history.

(56) References Cited

U.S. PATENT DOCUMENTS

| | | | |
|---|---|---|---|
| 4,098,728 A | 7/1978 | Rosenblatt | |
| 4,211,227 A | 7/1980 | Anderson et al. | |
| 4,636,208 A | 1/1987 | Rath | |
| 5,180,375 A | 1/1993 | Feibus | |
| 5,739,236 A | 4/1998 | Bowers et al. | |
| 5,866,113 A | 2/1999 | Hendriks et al. | |
| 6,054,504 A | 4/2000 | Dalla Riva Toma | |
| 6,150,459 A | 11/2000 | Mayes et al. | |
| 6,251,964 B1 | 6/2001 | Porssa et al. | |
| 6,284,854 B1 | 9/2001 | Bowers et al. | |
| 6,358,557 B1 | 3/2002 | Wang et al. | |
| 6,395,800 B1 | 5/2002 | Jones et al. | |
| 6,711,879 B2 | 3/2004 | Korteweg et al. | |
| 6,844,028 B2 | 1/2005 | Mao et al. | |
| 7,238,426 B2 | 7/2007 | Jiang et al. | |
| 7,276,286 B2 | 10/2007 | Chapman et al. | |
| 7,300,990 B2 | 11/2007 | Lewis et al. | |
| 7,306,625 B1 | 12/2007 | Stratford et al. | |
| 7,629,029 B2 | 12/2009 | Mao et al. | |
| 7,879,444 B2 * | 2/2011 | Jiang et al. | 428/411.1 |
| 2001/0050749 A1 | 12/2001 | Watanabe | |
| 2003/0021823 A1 | 1/2003 | Landers et al. | |
| 2004/0256232 A1 | 12/2004 | Jiang et al. | |
| 2006/0057180 A1 | 3/2006 | Chilkoti et al. | |
| 2006/0217285 A1 | 9/2006 | Destarac | |
| 2007/0048249 A1 | 3/2007 | Youngblood et al. | |
| 2007/0254006 A1 | 11/2007 | Loose et al. | |
| 2008/0181861 A1 | 7/2008 | Jiang et al. | |
| 2008/0286332 A1 | 11/2008 | Pacetti | |
| 2009/0155335 A1 | 6/2009 | O'Shaughnessey et al. | |
| 2009/0197791 A1 | 8/2009 | Balastre et al. | |
| 2009/0259015 A1 | 10/2009 | Jiang et al. | |
| 2010/0072642 A1 | 3/2010 | Broad et al. | |
| 2010/0099160 A1 | 4/2010 | Jiang et al. | |

FOREIGN PATENT DOCUMENTS

| | | |
|---|---|---|
| WO | 95/05408 A1 | 2/1995 |
| WO | 03/000433 A1 | 1/2003 |
| WO | 2007/002493 | 1/2007 |
| WO | 2007/024393 A2 | 3/2007 |
| WO | WO 2007/095393 * | 8/2007 |
| WO | 2008/006911 | 1/2008 |
| WO | 2008/006911 A1 | 1/2008 |
| WO | 2008/019381 A1 | 2/2008 |
| WO | 2008/083390 A2 | 7/2008 |

(Continued)

OTHER PUBLICATIONS

Cheng et al (Inhibition of bacterial adhesion and biofilm formation on zwitterionic surfaces, Biomaterials 28 (2007) 4192-4199).*
Jun, et al., "Surface modification of segmented poly(ether urethane) by grafting sulfo ammonium zwitterionic monomer to improve hemocompatibilities," Colloids and Surfaces B: Biointerfaces, 28(1):1-9 (2003).
Kildal, et al., "Peroxide-initiated grafting of acrylamide on to polyethylene surfaces," J. Appl. Pol. Sci., 44: 1893-8 (1992).
West, et al., "The biocompatibility of crosslinkable copolymer coatings containing sulfobetaines and phosphobetaines", Biomaterials, 25(7-8):1195-1204 (2004).

(Continued)

*Primary Examiner* — Suzanne Ziska
(74) *Attorney, Agent, or Firm* — Bryan Cave LLP

(57) ABSTRACT

Substrates, optionally coated with an undercoating, having grafted thereto one or more non-fouling materials are described herein. The non-fouling, polymeric material can be grafted to a variety of functionalized substrate materials, particularly polymeric substrates and/or polymeric undercoatings immobilized on a substrate. The compositions described herein are highly resistant protein absorption, particularly in complex media and retain a high degree of non-fouling activity over long periods of time. The compositions described herein may also demonstrate antimicrobial and/or antithrombogenic activity. The non-fouling material can be grafted to a functionalized substrate, or optionally from an undercoating on the substrate, preferably without significantly affecting the mechanical and/or physical properties of the substrate material.

38 Claims, No Drawings

FOREIGN PATENT DOCUMENTS

WO 2009/085096 A2 7/2009

OTHER PUBLICATIONS

Zhang, et al., "Surface Grafted Sulfobetaine Polymers via Atom Transfer Radical Polymerization as Superlow Fouling Coatings", Journal of Physical Chemistry B, 110:10799-10804 (2006).

Zhang, et al., "Superlow Fouling Sulfobetaine and Carboxybdaine Polymers on Glass Slides", Langmuir 22(24)10072-10077 (2006).

Bell, et al., Bionmedical membranes from hydrogels and interpolymer complexes, Biopolymers II, 1995, 122, 125-175.

Cheng et al. Zwitterionic carboxybetaine polymer surfaces and their resistance to long-term biofilm formation, Biomaterials, 2009, 30(28), 5234-5240.

Chapman et al., Polymeric thin films that resist the adsorption of proteins and the adhesion of bacteria, Langmuir, 2001, 17(4), 1225-1233.

Du et al., Grafted poly-(ethylene glycol) on lipid surfaces inhibits protein adsorption and cell adhesiion, Biochimica et Biophysica Acta (BBA)—Biomembrances, 1997, 1326(2), 236-248.

Harder et al., Conformation in Oligo(ethylene glycol)-terminated self-assembled monolayers on gold and silver surfaces determines their ability to resist protein adsorption, The Journal of Physical Chemistry B, 1998, 102(2), 426-436.

Haynie et al., Antimicrobial activities of amphipilic peptides covalently bonded to a water-insoluble resin, Antimicrobial Agents and Chemotherapy, 1995, 39(2), 301-307.

Ignatova et al., Combination of electrografting and atom-transfer radical polymerization for making the stainless steel surface antibacterial and protein antiadhesive, Langmuir, 2005, 22(1), 255-262.

Yuan et al., Improvement of blood compatibility on cellulose membrane surface by grafting betaines, Colloids and Surfaces B: Biointerfaces, Mar. 20, 2003, 147-155.

Lowe et al., Well-defined sulfobetaine-based statistical copolymers as potential antibioadherent coatings, J. Biomed Mater Res, 2000, 52, 88-94.

Massia et al., Immobilized RGD peptides on surface-grated dextran promote biospecific cell attachment., J. Biomed Mater res, 2001, 56(3), 390-399.

Michel et al., Influence of PEG architecture on protein adsorption and conformation, Langmuir, 2005, 21(26), 12327-12332.

Sakharov et al., Caralytic oxidative deformylation of polyethylene glycols with the participation of molecular oxygen, Kinetics and Catalysis, 2001, 42(5), 662-668.

Tada et al., Anti-biofouling properties of polymers with a carboxybetaine moiety, Macromolecular Biosciences, 2009, 9(1), 53-70.

Wang et al., Antifouling ultrafiltration membrane composed of polyethersulfone and sulfobetaine copolymer, Journal of membrane Science, 2006, 280, 343-350.

Jiang, Zwitterionic Separation Materials for Liquid Chromatography and Capillary Electrophoresis Synthesis, Characterization and Application for Inorganic Ion and Biomolecule Separations, PhD Dissertation, Umeå University, Umeå, Sweden, 63 pages, 2003.

Zhang et al., Blood compatibility of surfaces with superilow protein adsorption, Biomaterials, 2008, 29(32), 4285-4291.

International Search Report issued in PCT/US09/67007 on May 7, 2010, 3 pages.

* cited by examiner

LAYERED NON-FOULING, ANTIMICROBIAL ANTITHROMBOGENIC COATINGS

CROSS-REFERENCE TO RELATED APPLICATIONS

This applications claimed priority to U.S. Ser. No. 61/120,285 entitled "Synthetic Anticoagulant and Antithrombogenic Polymers" by Zheng Zhang, William Shannan O'Shaughnessy, Michael Hencke, Trevor Squier, and Christopher Loose, filed Dec. 5, 2008; U.S. Ser. No. 61/120,292 entitled "Presentation of Immobilized Molecules" by William Shannan O'Shaughnessy, Victoria E. Wagner Sinha, Zheng Zhang, Michael Hencke, Trevor Squier, and Christopher Loose, filed Dec. 5, 2008; U.S. Ser. No. 61/120,302 entitled "Layered Antimicrobial and Antithrombogenic Coatings" by Zheng Zhang, William Shannan O'Shaughnessy, Michael Hencke, Trevor Squier, Michael Bouchard, and Christopher Loose, filed Dec. 5, 2008; and U.S. Ser. No. 61/255,264 entitled "Layered Antimicrobial and Antithrombogenic Coatings" by Zheng Zhang, William Shannan O'Shaughnessy, Michael Hencke, Trevor Squier, Michael Bouchard, and Christopher Loose, filed Oct. 27, 2009.

FIELD OF THE INVENTION

The present invention is in the field of immobilized non-fouling coatings, specifically coatings that resist the adhesion of biological material and are attached to a substrate surface through a graft to method.

BACKGROUND OF THE INVENTION

Many different materials have been investigated to resist non-specific protein adsorption. Chemistries utilized for this purpose include polyethers (e.g., polyethylene glycol in particular), polysaccharides such as dextran, hydrophilic polymers such as polyvinylpyrrolidone or hydroxyethyl-methacrylate, heparin, intramolecular zwitterions or mixed charge materials, and hydrogen bond accepting groups such as those described in U.S. Pat. No. 7,276,286. The ability of these materials in preventing protein adsorption varies greatly between the chemistries. Of these materials, only a few resist fouling to the degree required for short-term in vivo application. However, the few materials appropriate for short-term application, when used for longer periods of time in complex media or in vivo, exhibit significant fouling or material degradation, making them unsuitable for long-term applications.

Traditional application of biocompatible coatings, especially those applied to medical device substrates, is performed by dip coating the substrate in a single polymer solution. For hydrophilic polymers applied to hydrophobic substrates, this approach presents many challenges as it can be difficult to form stable coatings. In an attempt to improve stability, hydrophilic materials have been cross-linked or copolymerized with hydrophobic groups. However, such approaches can have significant negative effects on the overall coating performance, especially when resistance to protein adsorption is desired.

There exists a need for coating formulations that overcome the limitations described above.

Therefore, it is an object of the invention to provide non-fouling coating formulations where an undercoating functionalized substrate is used to promote adhesion of a top coating onto a substrate surface and methods of making and using thereof.

SUMMARY OF THE INVENTION

Functionalized substrates, optionally coated with one more undercoats, having grafted thereto one or more non-fouling polymeric materials are described herein. Non-fouling coatings with varying tether chemistry or polymer backbone chemistry provide an alternative approach to developing highly efficient, biocompatible, and bioresponsive non-fouling coatings. In a preferred embodiment, the coatings are non-leaching. Conventional fouling resistant or non-fouling materials and surface coatings are susceptible to fouling over prolonged exposure to complex media or in vivo environments. The materials used for many non-fouling and fouling resistant coatings, or the tethers used to immobilize the coatings on a substrate, do not posses the stability required to coat the substrate for extended periods of time, for example, at least 7, 14, 30, 60, 90, 120, 365, or 1000 days The top coating can be immobilized directly to a functionalized substrate, optionally containing an undercoating, using dispersive, covalent, coordinate, ionic or chelation type bonding. Alternatively, the top coating can be immobilized using small molecule tethers, which are covalently or non-covalently attached to the undercoating. The bonding between the top coating and the small molecule tethers can be dispersive, covalent, coordinate, ionic or chelation type bonding. In another embodiment the top coating is immobilized directly on the substrate surface through dispersion, covalent, coordinate, ionic, or chelation type bonding. The top coating or top coating set can be reacted with an undercoating or undercoating set before being applied or immobilized to the substrate surface. Alternatively, the undercoating can be immobilized on the substrate surface followed by immobilization of the top coating on the undercoating.

In one embodiment, a composition containing an undercoating, immobilized on a substrate or on top of one or more preceding coatings on the substrate, through covalent, coordinate, dispersive, or chelation type bonding is coated with a top coating that is attached to the undercoating through covalent, coordinate, dispersive, or chelation type bonding. By functionalizing the substrate with an undercoating to aid in the attachment of the non-fouling topcoat, superior non-fouling performance may be achieved. For example, having an undercoating presenting reactive functional groups can allow for a minority of complementary reactive functional groups in the topcoat to stably bind the topcoat. The majority of the groups in the topcoat can be non-fouling groups. Having a high fraction of non-fouling groups in the topcoat may improve non-fouling performance. Optionally, this high non-fouling performance is achieved with stability achieved through the covalent binding of the topcoat to the undercoat or functionalized substrate.

In other embodiments, the non-fouling polymeric materials described herein can be applied as a top coating over an undercoating such that the non-fouling coating degrades or does not degrade, revealing or protecting, respectively, the coating or coatings below the top coating. Many existing non-fouling materials or tethers also contain labile functional groups that react in vivo resulting in arbitrary degradation of the material or release of the coating from the substrate, exposing the underlying surface. An exposed substrate is more likely to foul and, in the case of blood contacting devices, could result in thrombus formation. In contrast to the methods previously relied upon for creating fouling resistant and non-fouling coatings, the polymer and tether chemistries described herein not only allow for the creation of stable non-fouling surface coatings, but also allow for tailoring the reactivity of the coatings to respond to changes in a given environment (e.g anti-inflammatory drug release, during an oxidative burst, at a site of injury).

In other embodiments, linkers used to immobilize the coating(s) are responsive to the surrounding environment; for example, the coating is released or releases an encapsulated bioactive agent only under specific environmental changes, such as in the case of oxidative conditions, low pH, high pH, temperature changes, exposure to radiation, including, but not limited to microwave radiation, ultraviolet radiation, or X-ray radiation, or at a site of interest and does not release coating or agent at any other time.

In alternative embodiments, the responsive linker can re-capture or re-immobilize the coating or bioactive agent, which may be present in the surrounding solution or retained within the device. The linking system that responds to changes in physiological conditions can be used to attach the top coating to the undercoating; to attach the undercoating to the substrate surface; and/or to attach the undercoating to the substrate and the top coating to the undercoating.

In another embodiment the undercoating(s) are immobilized through polymer chain entanglements with the substrate surface and the top coating is attached to undercoating through covalent, coordinate, dispersive, or chelation type bonding.

In other embodiments, the undercoating is incorporated into the bulk substrate material, and the top coating is attached to the undercoating through covalent, coordinate, dispersive, ionic, or chelation type bonding. The top coating itself can be immobilized through chain entanglements directly with the substrate surface.

In one embodiment, the top coating contains a polymer containing a tethering segment where the tethering segment contains one or more reactive groups that can participate in covalent, coordinate, dispersive, ionic or chelation type bonding with the undercoating. In a particular embodiment, the top coat contains the tethering segment polyglycidyl methacrylate, and a non-fouling segment, for example, a zwitterionic polymeric material, such as polysulfobetaine, polycarboxybetaine or combinations thereof. In a preferred embodiment, the undercoat is a copolymer of glycidyl methacrylate methacrylate (GMA), 2-hydroxypropyl methacrylate (HPMA), lauryl methacrylate (LMA), and trimethoxysilyl methacrylate (TMOSMA) and the topcoat is a copolymer of carboxybetaine methacrylate (CBMA) and 2-aminoethyl methacrylate (AEMA) or a copolymer of sulfobetaine methacrylate (SBMA), glycidyl methacrylate methacrylate, and 2-hydroxypropyl methacrylate. In another preferred embodiment, the undercoating is a copolymer of 2-aminoethyl methacrylate (AEMA), 2-hydroxypropyl methacrylate (HPMA), lauryl methacrylate (LMA), and trimethoxysilyl methacrylate (TMOSMA) and the topcoat is a copolymer of carboxybetaine or sulfobetaine methacrylate and glycidyl methacrylate methacrylate.

The undercoatings and/or top coatings can be applied using a combination of chemistries known in the art including, but not limited to, aminolysis of the substrate which exposes reactive amines available for covalent or non-covalent bonding, click chemistry methods wherein the surface for attachment contains azide or terminal alkyne functionality and the coating to be immobilized contains either azide or terminal alkyne functionality wherein the surface for attachment does not contain the same functionality as the coating to be immobilized, and immobilization through thiol reactions involving olefins, alpha,beta-unsaturated carbonyls, or other thiols as in the case of disulfide bonding. Other chemistries can include anionic or cationic reactions, attachment of a nucleophile to an electrophile or attachment of an electrophile to nucleophile, and ring opening methods as in the case of an epoxide or aziridine, metathesis reactions. Organometallic reactions include chelation type bonding between a mono- or multidentate organic ligand and an inorganic atom with empty d-orbitals available for bonding. In some embodiments the chemistries used to immobilize a coating or coating set can be catalyzed or un-catalyzed.

Using assays discussed herein, coating formulations can be optimized to maximize anti-thrombotic, antimicrobial, and and/or anti-adherent properties of substrate materials, such as materials used to prepare catheters. For example, for topcoats, the ratio of CBMA to AEMA monomers can be varied from 1:1 to 20:1 to provide maximum protein resistance while still ensuring stable immobilization to the undercoat. NMR analysis (both proton and carbon) can be used to determine the ratio of monomer units incorporated into the polymer. The effect of top coat average molecular weight from 5K to 500K can be evaluated using dialysis and precipitation of top coat formulations. Effects of molecular weight distribution can be examined using varying free radical initiation schemes including uncontrolled initiation (which will provide a polydispersity >1.5) and highly controlled initiation through atom transferred radical polymerization (which typically provide a polydispersity <1.1). Gas permeation chromatography (GPC) with refractive index (RI) can be used to measure the molecular weight distribution of coatings materials.

The compositions described herein resist preferably greater than 50%, 55%, 60%, 65%, 70%, 75%, 80%, 85%, 90%, 95%, 99%, or 99.9% of the adsorption of protein from solution, for example phosphate buffered saline (PBS) containing protein, media, serum, or in vivo relative to an uncoated control for 1 day, 7 days, 14, 21, 30, 45, 60, 90, 120, 180, 365, or 1000 days.

The compositions described herein are stable over extended periods of time, retaining greater than 25%, 30%, 35%, 40%, 45%, 50%, 55%, 60%, 65%, 70%, 75%, 80%, 85%, 90%, 95%, or 99% of their non-fouling, anti-thrombotic, and/or antimicrobial properties for extended periods of time, for example, at least 1, 7, 14, 21, 30, 45, 60, 90, 120, 180, 365, or 1000 days.

The non-fouling material can be grafted to the undercoating without significantly affecting the mechanical and/or physical properties of the substrate material. In one embodiment, the tensile strength, modulus, device dimensions, or combinations thereof of the coated substrate are within 20%, preferably within 10%, more preferably within 5%, most preferably within 1% of the tensile strength, modulus, device dimensions, or combinations thereof of the uncoated substrate.

DETAILED DESCRIPTION OF THE INVENTION

I. Definitions

"Zwitterion" or "zwitterionic material" refers to a macromolecule, material, or moiety possessing both cationic and anionic groups. In most cases, these charged groups are balanced, resulting in a material with zero net charge. Zwitterionic polymers may include both polyampholytes (e.g, polymers with the charged groups on different monomer units) and polybetaine (polymers with the anionic and cationic groups on the same monomer unit).

"Polymer", as used herein, includes homopolymers and copolymers.

"Co-polymer", as used herein, refers to any polymer composed of one or more different monomers. The copolymer may be a random copolymer or block copolymer, such as an AB or ABA block copolymer or a graft copolymer.

"Antimicrobial" as used herein, refers to molecules and/or compositions that kill (i.e., bactericidal), inhibit the growth of (i.e., bacteristatic), and/or prevent fouling by, microorganisms including bacteria, yeast, fungi, mycoplasma, viruses or virus infected cells, cancerous cells, and/or protozoa.

Antimicrobial activity with respect to bacteria may be quantified using a colonization assay pre-incubation with 50% fetal bovine serum for 18-20 hours at 120 RPM at 37° C., which is preferred. Following pre-incubation, samples are placed in *Staphylococcus aureus* (*S. aureus*, ATCC 25923) which has been diluted from an overnight culture to a planktonic concentration of $1-3\times10^5$ CFU/mL in 1% tryptone soy broth (TSB). Samples are incubated with bacteria for 24-26 hrs with agitation (120 rpm) at 37° C. The concentration of TSB varies with the organism being used. After incubation, the samples are placed in 3 ml PBS for 5 min at 240 RPM at 37° C. to remove bacteria not tightly attached. Then accumulated bacteria on materials are removed by sonication in a new solution of PBS and the total number of bacterial cells quantified through dilution plating. Preferably at least a 1, 2, 3 or 4 log reduction in bacterial count occurs relative to colonization on a control. Similar adherence assays are known in the art for assessing platelet, cell, or other material adhesion to the surface. A surface that has a lower bacterial count on it than on reference polymers may be said to reduce microbial colonization.

"Anti-thrombogenic", as used herein, refers to the ability of a composition to resist thrombus formation. Anti-thrombogenic activity can be evaluated using ex-vivo flow loop model of thrombosis. Briefly, up to 10 liters of fresh blood are collected from a single animal. This blood is heparinised to prevent coagulation, filtered to remove particulates, and autologous radio-labeled platelets are added. Within eight hours after blood harvesting, coated and uncoated substrates are placed in a flow loop circuit, which pumps blood from a bath over the substrate and then back into the bath. A second internal flow loop circuit can be established for substrate containing a lumen by connecting the two ports of the substrate through a 2nd peristaltic pump. Blood is pumped in the outer circuit at a rate of approximately 2.5 L/min, while blood in the inner circuit is pumped at a rate of approximately 200-400 ml/min. After two hours, the substrates are removed, inspected visually for thrombus formation, and adhered platelets quantified using a Gamma counter. For samples not containing a lumen, only an outer circuit may be used to measure thrombus on the outside of the device.

"Adhesion", as used herein, refers to the non-covalent or covalent attachment of proteins, cells, or other substances to a surface. The amount of adhered substance may be quantified for proteins using the assay for non-fouling activity or for bacteria with the assay for antimicrobial activity or other relevant assays.

"Bioactive agent" or "active agent" or "biomolecule", used here synonymously, refers to any organic or inorganic therapeutic, prophylactic or diagnostic agent that actively or passively influences a biological system. For example, a bioactive agent can be an amino acid, antimicrobial peptide, immunoglobulin, an activating, signaling or signal amplifying molecule, including, but not limited to, a protein kinase, a cytokine, a chemokine, an interferon, tumor necrosis factor, growth factor, growth factor inhibitor, hormone, enzyme, receptor-targeting ligand, gene silencing agent, ambisense, antisense, an RNA, a living cell, cohesin, laminin, fibronectin, fibrinogen, osteocalcin, osteopontin, or osteoprotegerin. Bioactive agents can be proteins, glycoproteins, peptides, oligliopeptides, polypeptides, inorganic compounds, organometallic compounds, organic compounds or any synthetic or natural, chemical or biological compound.

"Non-fouling", as used herein, means that the composition reduces or prevents the amount of adhesion of proteins, including blood proteins, plasma, cells, tissue and/or microbes to the substrate relative to the amount of adhesion to a reference polymer such as polyurethane. Preferably, a device surface will be substantially non-fouling in the presence of human blood. Preferably the amount of adhesion will be decreased at least 20%, 25%, 30%, 35%, 40%, 45%, 50%, 55%, 60%, 65%, 70%, 75%, 80%, 85%, 90%, 95%, 99%, 99.5%, or 99.9% relative to the reference polymer.

Non-fouling activity with respect to protein, also referred to as "protein resistance" may be measured using an ELISA assay. For example, the ability of a composition to prevent the adhesion of blood proteins can be evaluated by measuring fibrinogen absorption through ELISA. Fibrinogen is a blood protein commonly used to assess the ability of a non-fouling surface to resist adsorption, given its important role in mediating platelet and other cell attachment. Briefly, samples are incubated for 90 minutes at 37° C. in 1 mg/mL fibrinogen derived from human plasma, then rinsed three times with 1×PBS and transferred to clean wells. The samples are incubated for another 90 minutes at 37° C. in 10% (v/v) fetal bovine serum to block the areas unoccupied by fibrinogen. The samples are rinsed, transferred to clean wells, and incubated for 1 hour with 5.5 ug/mL horseradish peroxidase conjugated anti-fibrinogen in 10% (v/v) fetal bovine serum. Again the samples are rinsed and transferred to clean wells with 0.1M phosphate-citrate buffer containing 1 mg/mL chromogen of o-phenylenediamine and 0.02% (v/v) hydrogen peroxide. Incubating at 37° C. for 20 minutes produces an enzyme-induced color reaction, which is terminated by the addition of 2.0N sulfuric acid. The absorbance of light intensity can then be measured using a microplate reader to determine the protein adsorption relative to controls. Preferably the amount of adhesion will be decreased at least 20%, 25%, 30%, 35%, 40%, 45%, 50%, 55%, 60%, 65%, 70%, 75%, 80%, 85%, 90%, 95%, 99%, 99.5%, or 99.9% relative to the reference polymer. For mixed protein solutions, such as whole plasma, surface plasmon resonance (SPR) or optical waveguide lightmode spectroscopy (OWLS) can be utilized to measure surface protein adsorption without necessitating the use of individual antigens for each protein present in solution. Additionally, radiolabeled proteins may be quantified on the surface after adsorption from either one protein or complex mixtures.

"Biocompatibility" is the ability of a material to perform with an appropriate host response in a specific situation. This can be evaluated using International Standard ISO 10993. Biocompatible compositions described herein are preferably substantially non-toxic. "Substantially non-toxic", as used herein, means a surface that is substantially hemocompatible and substantially non-cytotoxic.

"Substantially Non-Cytotoxic", as used herein, refers to a composition that changes the metabolism, proliferation, or viability of mammalian cells that contact the surface of the composition. These may be quantified by the International Standard ISO 10993-5 which defines three main tests to assess the cytotoxicity of materials including the extract test, the direct contact test and the indirect contact test.

"Substantially hemocompatible", as used herein, means that the composition is substantially non-hemolytic, in addition to being non-thrombogenic and non-immunogenic, as tested by appropriately selected assays for thrombosis, coagulation, and complement activation as described in ISO 10993-4.

"A substantially non-hemolytic surface", as used herein, means that the composition does not lyse 50%, preferably 20%, more preferably 10%, even more preferably 5%, most preferably 1%, of human red blood cells when the following assay is applied: A stock of 10% washed pooled red blood cells (Rockland Immunochemicals Inc, Gilbertsville, Pa.) is diluted to 0.25% with a hemolysis buffer of 150 mM NaCl and 10 mM Tris at pH 7.0. A 0.5 cm$^2$ antimicrobial sample is incubated with 0.75 ml of 0.25% red blood cell suspension for 1 hour at 37° C. The solid sample is removed and cells spun down at 6000 g, the supernatant removed, and the OD414 measured on a spectrophotometer. Total hemolysis is defined by diluting 10% of washed pooled red blood cells to 0.25% in sterile deionized (DI) water and incubating for 1 hour at 37° C., and 0% hemolysis is defined using a suspension of 0.25% red blood cells in hemolysis buffer without a solid sample.

"Complex media", as used herein, refers to biological fluids or solutions containing proteins or digests of biological materials. Examples include, but are not limited to, cation-adjusted Mueller Hinton broth, tryptic soy broth, brain heart infusion, or any number of complex media, as well as any biological fluid.

"Biological fluids" are fluids produced by organisms containing proteins and/or cells, as well as fluids and excretions from microbes. This includes, but is not limited to, blood, saliva, urine, cerebrospinal fluid, tears, semen, and lymph, or any derivative thereof (e.g., serum, plasma).

"Brush" or "Polymer Brush" are used herein synonymously and refer to polymer chains that are bound to a surface generally through a single point of attachment. The polymers can be end-grafted (attached via a terminal group) or attached via a side chain or a position in the polymer chain other than a terminal position. The polymers can be linear or branched. For example, the polymer chains described herein can contain a plurality of side chains that contain non-fouling groups. The side chains can consist of a single non-fouling moiety or monomer and/or a non-fouling oligomer (e.g., 2-10 monomers) or polymer (e.g., >10 monomers).

"Branch" and "Branched tether," are used interchangeably and refer to a polymer structure which originates from a single polymer chain but terminates in two or more polymer chains. The polymer may be a homopolymer or copolymer. Branched tether polymer structures may be ordered or random, may be composed, in whole or in part, of a non-fouling material, and may be utilized to immobilize one or more bioactive agents. In one embodiment, the branched tether is a dendrimer. A branched tether may be immobilized directly to a substrate or to an undercoating covering a substrate.

"Degradation products" are atoms, radicals, cations, anions, or molecules which are formed as the result of hydrolytic, oxidative, enzymatic, or other chemical processes.

"Density", as used herein, refers to the mass of material including, but not limited to, non-fouling materials and bioactive agents, that is immobilized per surface area of substrate.

"Inter-polymer chain distance", as used herein, refers to the distance between non-fouling polymer chains on the surface of the substrate or undercoating. Preferably, this distance is such that the non-fouling chains decrease the penetration of fouling materials into the coating material.

"Effective surface density", as used herein, means the range of densities suitable to achieve an intended surface effect including, but not limited to, antimicrobial or non-fouling activity, as defined herein.

"Hydrophilic" refers to polymers, materials, or functional groups which have an affinity for water. Such materials typically include one or more hydrophilic functional groups, such as hydroxyl, zwitterionic, carboxy, amino, amide, phosphate, hydrogen bond forming, and/or ether groups.

"Immobilization" or "immobilized", as used herein, refers to a material or bioactive agent that is covalently or non-covalently attached directly or indirectly to a substrate. "Co-immobilization" refers to immobilization of two or more agents.

"Non-degradable" as used herein, refers to material compositions that do not react significantly within a biological environment either hydrolytically, reductively, enzymatically or oxidatively to cleave into smaller or simpler components.

"Stable", as used herein, refers to materials which retain greater than 25%, 30%, 35%, 40%, 45%, 50%, 55%, 60%, 65%, 70%, 75%, 80%, 85%, 90%, 95%, or 99% of their original material properties such as surface contact angle, non-fouling, anti-thrombogenic, and/or antimicrobial activity for a time of 1, 7, 14, 30, 90, 365, or 1000 days in PBS containing protein, media, serum, or in vivo.

"Substrate", as used herein, refers to the material on which the undercoating is applied, or which is formed all or in part of non-fouling material, or on which the non-fouling and/or therapeutic, diagnostic, and/or prophylactic agents are immobilized.

"Coating", as used herein, refers to any temporary, semi-permanent or permanent layer, or layers, treating or covering a surface. The coating may be a chemical modification of the underlying substrate or may involve the addition of new materials to the surface of the substrate. It includes any increase in thickness to the substrate or change in surface chemical composition of the substrate. A coating can be a gas, vapor, liquid, paste, semi-solid or solid. In addition, a coating can be applied as a liquid and solidified into a solid coating.

"Undercoat" or "Undercoating," as used herein, refers to any coating, combination of coatings, or functionalized layer covering an entire substrate surface or a portion thereof under an additional coating. In one embodiment, the undercoating is used to alter the properties of one or more subsequent coatings or layers. The undercoating may be formed from a polymer or copolymer. In a preferred embodiment, the undercoat is used to aid in the immobilization of a topcoat on a substrate.

"Undercoating set," as used herein, refers to a set or group of one or more coatings under the top coating. This group or set of coatings can be applied together or separately covering an entire substrate surface or a portion thereof.

"Topcoat" or "Top coating," as used herein, refers to any coating, combination of coatings, or functionalized layer applied on top of one or more undercoatings, another top coating, or directly to a substrate surface. A top coating may or may not be the final coating applied to a substrate surface. In one embodiment a top coat is covalently attached to an undercoating. In another embodiment a top coating is encapsulated in a protective coating, which helps extend the top coatings storage life. In a preferred embodiment, the topcoat includes polymeric material.

"Top coating set," as used herein, refers to a set or group of one or more coatings on top of one or more undercoatings.

"Functionalized substrate", as used herein, refers to a substrate on which the number of reactive or functional groups has been increased and/or the identity of functional groups has been changed. This may be accomplished by making chemical alterations on the surface with techniques including, but not limited to, aminolysis. In other embodiments, this may be accomplished by the addition of an undercoating or undercoating set which contains functional groups.

"Non-leaching" or "Substantially non-leaching", as used herein synonymously, means that the compositions retains greater than 50%, 55%, 60%, 65%, 70%, 75%, 80%, 85%, 90%, 95%, 99% of the immobilized coating and/or bioactive agent over the course of 7, 14, 30, 90, 365, or 1000 days in phosphate buffered saline (PBS), media, serum, or in vivo. This can be assessed using radiolabeled active agent.

"Tether" or "tethering agent" or "Linker", as used herein synonymously, refers to any molecule, or set of molecules, or polymer used to covalently immobilize one or more non-fouling materials, one or more bioactive agents, or combinations thereof on a material where the molecule remains as part of the final chemical composition. The tether can be either linear or branched with one or more sites for immobilizing bioactive agents. The tether can be any length. However, in one embodiment, the tether is greater than 3 angstroms in length. The tether may be non-fouling, such as a monomer, oligomer, or polymer or a non-fouling non-zwitterionic material. The tether may be immobilized directly on the substrate or on a polymer, either of which may be non-fouling.

"Non-naturally occurring amino acid", as used herein, refers to any amino acid that is not found in nature. Non-natural amino acids include any D-amino acids, amino acids with side chains that are not found in nature, and peptidomimetics. Examples of peptidomimetics include, but are not limited to, b-peptides, g-peptides, and d-peptides; oligomers having backbones which can adopt helical or sheet conformations, such as compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination. All of the amino acids in the human body, except glycine, exist as the D and L fowls. Nearly all of the amino acids occurring in nature are the L-forms. D-forms of the amino acids are not found in the proteins of higher organisms, but are present in some lower forms of life, such as in the cell walls of bacteria. They also are found in some antibiotics, among them, streptomycin, actinomycin, bacitracin, and tetracycline. These antibiotics can kill bacterial cells by interfering with the formation of proteins necessary for viability and reproduction. Non-naturally occurring amino acids also include residues, which have side chains that resist non-specific protein adsorption, which may be designed to enhance the presentation of the antimicrobial peptide in biological fluids, and/or polymerizable side chains, which enable the synthesis of polymer brushes using the non-natural amino acid residues within the peptides as monomeric units.

"Polypeptide", "peptide", and "oligopeptide" encompasses organic compounds composed of amino acids, whether natural, synthetic or mixtures thereof, that are linked together chemically by peptide bonds. Peptides typically contain 3 or more amino acids, preferably more than 9 and less than 150, more preferably less than 100, and most preferably between 9 and 51 amino acids. The polypeptides can be "exogenous," or "heterologous," i.e. production of peptides within an organism or cell that are not native to that organism or cell, such as human polypeptide produced by a bacterial cell. Exogenous also refers to substances that are not native to the cells and are added to the cells, as compared to endogenous materials, which are produced by the cells. The peptide bond involves a single covalent link between the carboxyl group (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

"Antimicrobial peptide" ("AmP"), as used herein, refers to oligopeptides, polypeptides, or peptidomimetics that kill (i.e., are bactericidal) or inhibit the growth of (i.e., are bacteristatic) microorganisms including bacteria, yeast, fungi, mycoplasma, viruses or virus infected cells, and/or protozoa.

"Coupling agent", as used herein, refers to any molecule or chemical substance which activates a chemical moiety, for example on a bioactive agent or on the material to which it will be attached, to allow for formation of a covalent or non-covalent bond between the bioactive agent and the material to which it will be attached, wherein the material does not remain in the final composition after attachment.

"Cysteine", as used herein, refers to the amino acid cysteine or a synthetic analogue thereof, wherein the analogue contains a free sulfhydryl group.

"Membrane-targeting antimicrobial agent", as used herein, refers to any antimicrobial agent that retains its bactericidal or bacteriostatic activity when immobilized on a substrate and can therefore be used to create an immobilized antimicrobial surface. In one embodiment, the membrane-targeting antimicrobial agent is an antimicrobial peptide, and in another embodiment it is a quaternary ammonium compound or polymer. "Immobilized bactericidal activity" as used herein, refers to the reduction in viable microorganisms including bacteria, yeast, fungi, mycoplasma, viruses or virus infected cells, and/or protozoa that contact the surface. For bacterial targets, bactericidal activity may be quantified as the reduction of viable bacteria based on the ASTM 2149 assay for immobilized antimicrobials, which may be scaled down for small samples as follows: an overnight culture of a target bacteria in a growth medium such as Cation Adjusted Mueller Hinton Broth, is diluted to approximately $1 \times 10^5$ cfu/ml in pH 7.4 Phosphate Buffered Saline using a predetermined calibration between OD600 and cell density. A 0.5 $cm^2$ sample of immobilized antimicrobial surface is added to 0.75 ml of the bacterial suspension. The sample should be covered by the liquid and should be incubated at 37° C. with a sufficient amount of mixing that the solid surface is seen to rotate through the liquid. After 1 hour of incubation, serial dilutions of the bacterial suspension are plated on agar plates and allowed to grow overnight for quantifying the viable cell concentration. Preferably at least a 1, 2, 3 or 4 log reduction in bacterial count occurs relative to a control of bacteria in phosphate buffered saline (PBS) without a solid sample.

The term "alkyl" refers to the radical of saturated or unsaturated aliphatic groups, including straight-chain alkyl, alkene, and alkyne groups, branched alkyl, alkene, or alkyne groups, cycloalkyl (alicyclic), cycloalkene, and cycloalkyne groups, alkyl, alkene, or alkyne substituted cycloalkyl, cycloalkene, or cycloalkyne groups, and cycloalkyl substituted alkyl, alkene, or alkyne groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 20 or fewer carbons, more preferably less than 10 carbons atoms, most preferably less than 7 carbon atoms. Likewise, preferred cycloalkyls have from 3-10 carbon atoms in their ring structure, and more preferably have 5, 6 or 7 carbons in the ring structure.

It will be understood that "substitution" or "substituted" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, but are not limited to, aryl, heteroaryl, hydroxyl, halogen, alkoxy, nitro, sulfhydryl, sulfonyl, amino (substituted and unsubstituted), acylamino, amido, alkylthio, carbonyl groups, such as esters, ketones, aldehydes, and carboxylic acids; thiolcarbonyl groups, sultanate, sulfate, sulfinylamino, sulfamoyl, and sulfoxido.

The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This polymers described herein are not intended to be limited in any manner by the permissible substituents of organic compounds.

II. Compositions

A. Substrates

The non-fouling material may be grafted to a variety of different undercoatings immobilized on a variety of different substrates. The undercoating can be immobilized covalently or non-covalently on the substrate. Examples of suitable substrate materials include, but are not limited to, metallic materials, ceramics, polymers, woven and non-woven fibers, inert materials such as silicon, and combinations thereof. In one embodiment, the substrate is a material other than gold or glass.

Suitable metallic materials include, but are not limited to, metals and alloys based on titanium, such as unalloyed titanium (ASTM F67) and titanium alloys, such as ASTM F1108, Ti-6Al-4V ELI (ASTM F136), Nitinol (ASTM F2063), nickel titanium alloys, and thermo-memory alloy materials; stainless steel (ASTM F138 and F139), tantalum (ASTM F560), palladium, zirconium, niobium, molybdenum, nickel-chrome, or certain cobalt alloys including Stellite, cobalt-chromium (Vitallium, ASTM F75 and Wrought cobalt-chromium (ASTM F90)), and cobalt-chromium-nickel alloys such as ELGILOY® and PHYNOX®.

Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

Suitable polymeric materials include, but are not limited to, polystyrene and substituted polystyrenes, polyalkylenes, such as polyethylene and polypropylene, poly(urethane)s, polyacrylates and polymethacrylates, polyacrylamides and polymethacrylamides, polyesters, polysiloxanes, polyethers, poly(orthoesters), poly(carbonates), poly(hydroxyalkanoate)s, polyfluorocarbons, PEEK, Teflon, silicones, epoxy resins, KEVLAR®, NOMEX®, DACRON®, nylon, polyalkenes, phenolic resins, PTFE, natural and synthetic elastomers, adhesives and sealants, polyolefins, polysulfones, polyacrylonitrile, biopolymers such as polysaccharides and natural latex copolymers thereof, and combinations thereof. In one embodiment the substrate is a medical grade polyurethane or CARBOTHANE®, aliphatic polycarbonate-based polyurethanes, available from Lubrizol Corporation, blended with appropriate extrusion agents and plasticizers, possibly one already approved by the FDA or other appropriate regulatory agency for use in vivo.

The substrates may optionally contain a radiopaque additive, such as barium sulfate or bismuth to aid in radiographic imaging.

Substrates may be in the form of, or form part of, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), surgical, medical or dental instruments, blood oxygenators, ventilators, pumps, drug delivery devices, tubing, wiring, electrodes, contraceptive devices, feminine hygiene products, endoscopes, grafts (including small diameter <6 mm), stents (including coronary, ureteral, renal, biliary, colorectal, esophageal, pulmonary, urethral, and vascular), stent grafts (including abdominal, thoracic, and peripheral vascular), pacemakers, implantable cardioverter-defibrillators, cardiac resynchronization therapy devices, cardiovascular device leads, ventricular assist devices and drivelines, heart valves, vena cava filters, endovascular coils, catheters (including central venous, peripheral central, midline, peripheral, tunneled, dialysis access, urinary, neurological, peritoneal, intra-aortic balloon pump, angioplasty balloon, diagnostic, interventional, drug delivery, etc.), catheter connectors and valves (including needleless connectors), intravenous delivery lines and manifolds, shunts, wound drains (internal or external including ventricular, ventriculoperitoneal, and lumboperitoneal), dialysis membranes, infusion ports, cochlear implants, endotracheal tubes, tracheostomy tubes, ventilator breathing tubes and circuits, guide wires, fluid collection bags, drug delivery bags and tubing, implantable sensors (e.g., intravascular, transdermal, intracranial), ophthalmic devices including contact lenses, orthopedic devices (including hip implants, knee implants, shoulder implants, spinal implants (including cervical plates systems, pedicle screw systems, interbody fusion devices, artificial disks, and other motion preservation devices), screws, plates, rivets, rods, intramedullary nails, bone cements, artificial tendons, and other prosthetics or fracture repair devices), dental implants, periodontal implants, breast implants, penile implants, maxillofacial implants, cosmetic implants, valves, appliances, scaffolding, suturing material, needles, hernia repair meshes, tension-free vaginal tape and vaginal slings, prosthetic neurological devices, tissue regeneration or cell culture devices, or other medical devices used within or in contact with the body or any portion of any of these.

In one embodiment, the substrate is a vascularly inserted catheter such as a peripherally inserted central catheter (PICC), central venous catheter (CVC), or hemodialysis catheter, venous valves, punctual plugs, and intra-ocular devices and implants. In another embodiment, the substrate is a vascularly inserted catheter formed from a medical grade polyurthethane or CARBOTHANE® or formed from a material coated with a medical grade polyurethane or CARBOTHANE®.

The non-fouling materials can also be added to paints and other coatings and filters to prevent mildew, bacterial contamination, and in other applications where it is desirable to prevent fouling, such as marine applications (ship hull coatings), fuel tanks, oil pipelines, industrial piping, pharmaceutical equipment, drug delivery devices such as inhalers, contact lenses, dental implants, coatings for in vivo sensors, textiles such as hospital drapes, gowns, or bedding, ventilation conduits, doorknobs, devices for separations, such as membranes for microbial suspension, biomolecule separation, protein fractionation, cell separation, waste water treatment, water purification, bioreactors, and food processing.

These materials can also be used to treat surfaces of fibers, particulates and films for the applications of textiles, additives, electric/optical appliances, packaging materials and colorants/inks.

1. Effective Surface Area

In addition to the chemical composition of the substrate, the micro- and nano-structure of the substrate surface may be useful to maximize the surface area available for undercoating attachment. For metallic and ceramic substrates, increased surface area can be created through surface roughening, for example by a random process such as plasma etching. Alternatively, the surface can be modified by controlled nano-patterning using photolithography. Polymeric substrates can also be roughened as with metallic and ceramic substrates. For alternative applications, creating a polished or smoother surface may enhance non-fouling properties of the material. The surface can be modified to enhance the attachment and stability of an undercoating or an undercoating set. Alternatively, the surface may be polished or smoothed to reduce surface area as this may reduce physical features which could trap fouling agents. Further, having a defined roughness with physical features of specified sizes and distributions may control the interaction of bacteria, proteins, or other fouling agents with the surface. Each of these roughness variants may be enhanced with the addition of a non-fouling coating.

2. Surface Microstructure

In the case where a greater density of non-fouling material is desired, the creation of microstructure on the undercoating can create more area for immobilizing the undercoating to the surface, without increasing the apparent surface area of the substrate. For polymeric substrates, including hydrogel networks, this surface morphology can be created through appropriate polymer structural design.

B. Undereoatings

The substrate has immobilized thereon one or more undercoatings. The undercoating can be immobilized covalently or non-covalently to the substrate surface. In some embodiment, the undercoating(s) are immobilized on the substrate through polymer chain entanglements with the substrate surface. Examples of non-covalent interactions include, but are not limited to, ionic bonds, coordination, dispersion, chelation, and combinations thereof. In those embodiments where the underlayer is covalently attached to the substrate, the undercoating can be immobilized directly on the substrate surface or through a linker or tether. The linker or tether can be part of the undercoating or can be grafted to or from the surface of the substrate prior to application of the undercoating.

One function of the undercoating is to provide reactive functional groups to immobilize the top coating. In preferred embodiments, one or more functional groups on the undercoating and one or more complimentary reactive functional groups in the topcoat may be used to immobilize the topcoat on the undercoat. A range of reactive functional groups are described below for both the undercoating and topcoat, though any reactive combination may be used. In preferred embodiments, the reactive combination includes, but is not limited to, epoxy-amine, isocyanate-carboxyl, glycidyl-anhydride, amine-anhydride, silanol-silanol, isocyanate-amine, carboxyl-amine, and hydroxyl-carboxyl groups.

Another function of the undercoating is to provide a uniform surface to which can be attached other coatings, tethers or linkers, and/or bioactive agents. For example, medical device substrates are often composed of multiple different materials, each with its own surface properties. Even devices composed of a single polymer are in fact made up of material blends and can include plasticizers, radio-opacity agents, and other additives all of which can affect substrate surface properties. In order to ensure surface uniformity for maximization of coating adhesion and efficacy, a precoat of a single polymer may be coated on the substrate. For example, a substrate can be coated with a polymer coating, such as polyurethane, followed by immobilization of one or more additional undercoatings and one or more top coatings on the undercoating(s). The polymer can be deposited on the substrate using a variety of techniques known in the art, such as solvent casting.

The undercoating should be mechanically stable and should not be dissolved, after curing, by the solvent used to apply the topcoat. In some embodiments, the undercoating is applied using a process that does no substantially impact the mechanical properties of the substrate. The solvent, temperature, and reaction times used during the application process may be selected to minimize the impact on the mechanical properties of the substrate.

The undercoating or undercoatings can be homopolymers or copolymers, such as random or block copolymers, formed by condensation or radical polymerization. Suitable monomers include, but are not limited to, acrylates, including substituted acrylates, such as hydroxyalkyl acrylates, acrylates with primary, secondary, or tertiary amino groups, alkyl methacrylates, and reactive or crosslinkable acrylate, such as acrylates containing silyl groups, double bonds, or other reactive functional groups; acrylamides, including substituted acrylamides as described above for acrylates; vinyl compounds; multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams; and combinations thereof. Exemplary monomers are listed below:

(1) Charged methacrylates or methacrylates with primary, secondary or tertiary amine groups, such as, 3-sulfopropyl methacrylate potassium salt, (2-dimethylamino)ethyl methacrylate) methyl chloride quaternary salt, [2-(methacryloyloxy)ethyl]trimethyl-ammonium chloride, methacryloyl chloride, [3-(methacryloylamino)propyl]-trimethylammonium chloride), 2-aminoethyl methacrylate hydrochloride, 2-(diethylamino)ethyl methacrylate, 2-(dimethylamino) ethyl methacrylate, 2-(tert-butylamino)ethyl methacrylate, and 2-(tert-butylamino-ethyl methacrylate.

(2) Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, 2-naphthyl methacrylate, 2,2,3,3-tetrafluoropropyl methacrylate, 1,1,1,3,3,3-hexafluoroisopropyl methacrylate, 2,2,2-trifluoroethyl methacrylate, 2,2,3,3,3-pentafluoropropyl methacrylate, 2,2,3,4,4,4-hexafluorobutyl methacrylate, 2,2,3,3,4,4,4-heptafluorobutyl methacrylate, 2,2,3,3,4,4,5,5-octafluoropentyl methacrylate, 3,3,4,4,5,5,6,6,7,7,8,8,8-tridecafluorooctyl methacrylate, and 3,3,4,4,5,5,6,6,7,7,8,8,9,9,10,10,10-heptadecafluorodecyl methacrylate.

(3) Reactive or crosslinkable methacrylates, such as 2-(trimethylsilyloxy)-ethylmethacrylate, 3-(trichlorosilyl)propyl methacrylate, 3-(trimethoxysilyl)-propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate, 3-(dimethylchlorosilyl)propyl methacrylate, isocyanates, such as 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

(4) Other methacrylates, such as ethylene glycol methyl ether methacrylate, di(ethylene glycol) methyl ether methacrylate, ethylene glycol phenyl ether methacrylate, 2-butoxyethyl methacrylate, 2-ethoxyethyl methacrylate, and ethylene glycol dicyclopentenyl ether methacrylate.

Condensation type monomers can also be used.

Acrylamide and/or methacrylamide of the monomers listed above can also be used, as well as other monomers with unsaturated bonds.

Multifunctional monomers, such di, tri, or tetraacrylates or substituted acrylates can be used to form highly branched structures which can provide a higher concentration of non-fouling groups.

In one embodiment, the undercoating is a copolymer of glycidyl methacrylate (GMA), 2-hydroxypropyl methacrylate (HPMA), lauryl methacrylate (LMA), and trimethoxysilyl methacrylate (TMOSMA). In another embodiment, the undercoating is a copolymer of 2-aminoethyl methacrylate (AEMA), 2-hydroxypropyl methacrylate (HPMA), lauryl methacrylate (LMA), and trimethoxysilyl methacrylate (TMOSMA).

C. Top Coating

The compositions described herein contain a top coating, which is immobilized on the outermost undercoating. The top coating can be biodegradable or non-biodegradable, revealing or protecting, respectively, the undercoating(s) underneath the top coating.

The top coating can be immobilized covalently or non-covalently. The top coating can be immobilized covalently to the undercoating(s) directly via covalent bond formation between reactive functional groups on the undercoating and the top coating. Alternatively, the top coating can be immobilized to the undercoating(s) via a tether or linker. The tether or linker can be immobilized on the undercoating(s) covalently or non-covalently and the top coating can be immobilized on the linker or tether covalently or non-covalently. The top coating can also be immobilized covalently or non-covalently on the substrate, in the absence of an undercoating(s).

Alternatively, reactive functional groups may be created on the substrate directly in order to provide reactive sites to bond with reactive functional groups in the topcoat. Suitable methods for creating reactive functional groups on the substrate are known in the art. Reactive functional groups, either on the substrate itself or on the undercoating, can be introduced, for example, by physical adsorption, chemical reaction, plasma treatment, and/or surface grafting methods.

Physical adsorption methods involve any small reactive agents which are pre-adsorbed or migrate to the surface by methods including, but not limited to, solvent imbibing, blending, and vapor deposition.

Chemical reaction methods to create reactive functional groups include, but are not limited to, amination, hydrolysis, and silanization.

Plasma treatment methods include, but are not limited to, inert gas, reactive gas, monomers, and plasma polymerization treatment.

Surface grafting methods include, but are not limited to, surface initiated reactions, such as polymerization, which include, but are not limited to, photo-initiated, thermal-initiated, redox-initiated, controlled free radical, and anionic and cationic reactions.

In one embodiment, the top coating contains a polymer containing one or more non-fouling segments and one or more tethering segments where the non-fouling segment is preferably greater than 25%, 30%, 35%, 40%, 45%, 50%, 55%, 60%, 65%, 70%, 75%, 80%, 85%, 90%, 95%, 99.0%, 99.5%, 99.9%, or 99.99% by molar ratio of the polymer.

Top coatings can be formed by synthetic means known in the art including, but not limited to, free radical polymerization (e.g., thermal, UV, and/or redox), ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET).

1. Non-Fouling Materials

Surfaces which resist non-specific protein adsorption are important in the development of biomedical materials, such as medical devices and implants. Such coatings limit the interactions between the implants and physiological fluids. In environments where fluids contain high concentrations of biological proteins, such as blood contacting applications, prevention of protein adsorption may prevent fouling of the device surface and/or thrombus formation. In one embodiment, the non-fouling material is a polymeric material. Suitable polymeric materials include, but are not limited to, zwitterionic polymers, non-zwitterionic polymers, and combinations thereof. The non-fouling polymeric material typically a has a weight average molecular weight from about 1,000 Daltons to 2,000,000 Daltons, preferably from 1,000 Daltons to about 1,000,000 Daltons, more preferably from about 1,000 Daltons to about 500,000 Daltons, most preferably 5,000 Daltons to about 500,000 Daltons.

i. Zwitterionic Materials

Zwitterions are molecules that carry formal positive and negative charges on non-adjacent atoms within the same molecule. Both natural and synthetic polymers, containing zwitterion functionality, have been shown to resist protein adhesion. In one embodiment, the zwitterionic monomer contains a phosphorylcholine moiety, a sulfobetaine moiety, a carboxy betaine moiety, derivatives thereof, or combinations thereof. Substrate surfaces treated with phosphorylcholine (PC), a natural zwitterionic molecule, not only exhibit reduced protein adsorption, but also exhibit increased blood compatibility, when compared to untreated substrate surfaces. Polymers created from phosphorylcholine are also considered biomimetic in addition to exhibiting the properties discussed above.

Sulfobetaine, closely resembles 2-aminoethanesulfonic acid, one of the most abundant, low molecular weight organic compounds found in animals. Sulfobetaine monomers are typically easier to handle than phosphorylcholine and the resulting polymers are generally easier to synthesize than the corresponding phosphorylcholine analogs.

Polycarboxybetaines are polymeric analogs of the naturally occurring zwitterion, glycine betaine. Similar to polyphosphorylcholines and polysulfobetaines, polycarboxybetaines are another class of zwitterionic, biomimetic polymers with exceptional resistance to biofouling. These polymers are particularly well suited for blood contacting applications due to anti-thrombogenic and anticoagulant properties unique to carboxybetaines. In addition to these properties, it is possible to design carboxybetaine monomers such that the resulting polymers contain reactive functional groups for immobilization of bioactive molecules. By creating carboxybetaine brushes on the surface, the dual function of resisting protein or platelet attachment and having an actively anticoagulant group may reduce thrombosis on a surface further than using either strategy alone.

Polysulfo- and polycarboxybetaines are not only biomimetic and highly resistant to bacterial adhesion, biofilm formation, and nonspecific protein adsorption from blood serum and plasma, they are also non-toxic, biocompatible and typically exhibit greater stability in complex media or in vivo when compared to both polyphosphorylcholine and polyethylene glycol), which may be degraded. The application of these materials and coatings can be further extended using biologically active agents, such as antimicrobial peptides.

Other natural and synthetic zwitterion chemistries can be used to design non-fouling materials for the biomedical applications described herein. Some examples of natural zwitterions chemistries that could be used for non-fouling materials include, but are not limited to, amino acids, peptides, natural small molecules including, but not limited to, N,N,N-trimethylglycine (glycine betaine), trimethylamine oxide (TMAO), dimethylsulfoniopropionate sarcosine, lysergic acid and psilocybin. Additional synthetic zwitterions that could be used to create non-fouling materials, include, but are not limited to, amino-carboxylic acids (carboxy betaines), amino-sulfonic acids (sulfo betaines), cocamidopropyl betaine, quinonoid based zwitterions, decaphenylferrocene, and non-natural amino acids. Natural and synthetic polymers also include mixed charged structures with both positive charged and negative charged moieties on the pendant groups, in the main chains, or at the terminal groups.

Materials containing, or composed of, these natural or synthetic zwitterions, can be applied to surfaces, particularly the surfaces of medical devices, in order to improve biocompatibility, reduce thrombogenesis (such as on the surface of stents or venous valves), and reduce fouling by proteins or bacteria present in solution. This is particularly applicable for surfaces where non-specific binding of proteins in solution could negatively impact the desired or necessary mechanics of a device.

In one embodiment, the non-fouling material is a zwitterionic polymer grafted from the substrate. For example, the polymer can contain one or more monomers of Formula I:

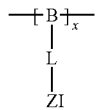

I wherein B is selected from the group consisting of:

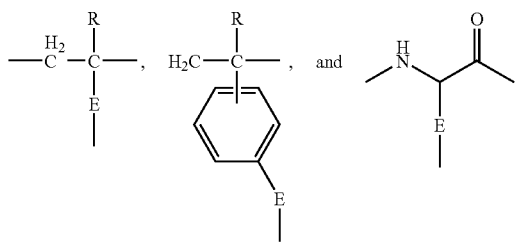

wherein R is selected from the group consisting of hydrogen, substituted alkyl, or unsubstituted alkyl;

E is selected from the group consisting of substituted alkyl, unsubstituted alkyl, —(CH$_2$)$_y$C(O)O—, and —(CH$_2$)$_y$C(O)NR$^2$;

Y is an integer from 0-12;

L is absent or is a straight or branched alkyl group optionally including one or more oxygen atoms;

ZI is a zwitterionic group; and

X is an integer from 3 to 1000.

In a particular embodiment, ZI is selected from the group consisting of

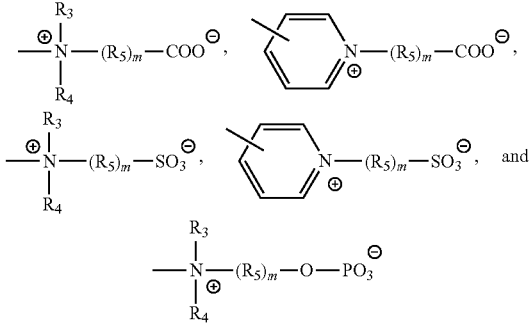

wherein R$_3$ and R$_4$ are independently selected from the group consisting of hydrogen and substituted or unsubstituted alkyl;

R$_5$ is selected from the group consisting of substituted or unsubstituted alkyl, phenyl, and polyether groups; and M is an integer from 1-7.

In another embodiment, the polymer contains one or more monomers of Formula II:

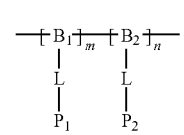

II wherein B$_1$ and B$_2$ are independently selected from

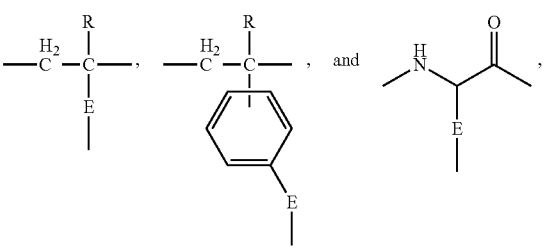

R is selected from hydrogen and substituted or unsubstituted alkyl;

E is selected from substituted or unsubstituted alkylene, —(CH$_2$)$_p$C(O)O—, and —(CH$_2$)$_p$C(O)NR$^2$—, wherein p is an integer from 0 to 12, R$^2$ is selected from hydrogen and substituted or unsubstituted alkyl;

L is a straight or branched alkylene group optionally including one or more oxygen atoms;

P$_1$ is a positively charged group;

P$_2$ is a negatively charged group, such as a carboxylate group or an SO$_3^-$ group;

m is an integer from 3 to 1000; and n is an integer from 3 to 1000.

In one embodiment, the positively charged group is a moiety containing a quaternary nitrogen or a cationic phosphorous group and the negatively charged group is a moiety containing a carboxylic acid group, $SO_3^-$, or $PO_3^-$ group.

In still another embodiment, the polymer contains one or monomers of Formula III, IV, or V:

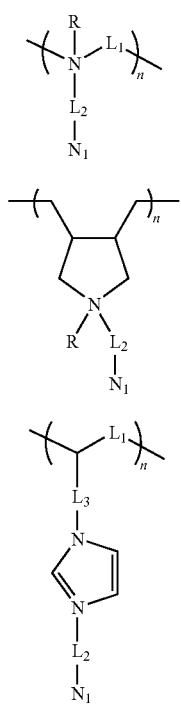

wherein R is selected from and substituted or unsubstituted alkyl;

$L_1$ $L_2$, and $L_3$ are independently a straight or branched alkylene group optionally including one or more oxygen atoms; and n is an integer from 3 to 1000; and N1 is a negatively charged group such as a carboxylate group, $SO_3^-$ group, or $PO_3^-$ group.

In certain embodiments, an antimicrobial and/or antithrombotic composition is provided, that contains a substrate, for example, polyurethane, covalently bound to a plurality of polymer chains. For example, such polymer chains may be represented by Formula I, II, III, IV, or V. In certain embodiments, the non-fouling material is a brush structure containing one or more monomers of Formula I, II, III, V, or V. In still other embodiments, a the non-fouling material is a copolymer containing one or more of the monomers represented by Formula I, II, III, IV, or V.

In certain embodiments, an antimicrobial and/or antithrombotic polymeric composition is provided, that contains an undercoat covalently bound to a plurality of homopolymer chains, wherein the polymer chains optionally contain one or more tethering segments. For example, such homopolymer chains may be represented by Formula I, II, III, or IV. In certain embodiments, the non-fouling material is a brush structure containing one or more monomers of Formula I, II, III, or IV. In still other embodiments, a the non-fouling material is a copolymer containing one or more of the monomers represented by Formula I, II, III, or IV.

In one embodiment, the topcoat is a copolymer of carboxybetaine and 2-aminoethyl methacrylate (AEMA) or a copolymer of sulfobetaine methacrylate, glycidyl methacrylate methacrylate, and 2-hydroxypropyl methacrylate.

ii. Non-Zwitterionic Non-Fouling Materials

The topcoating can also contain a non-zwitterionic non-fouling material, alone or in combination with a zwitterionic material. These non-fouling groups may have varying degrees of non-fouling performance in a range of environments. Suitable non-zwitterionic materials include, but are not limited to, polyethers (e.g., polyethylene glycol), polysaccharides such as Dextran, hydrophilic polymers such as polyvinylpyrrolidone (PVP) and hydroxyethyl-methacrylate (HEMA), heparin, mixed charge materials, and materials containing hydrogen bond accepting groups, such as those described in U.S. Pat. No. 7,276,286. Suitable polymer structures included, but are not limited to, polymers or copolymers containing monomers of Formula I wherein ZI is replaced by a non-zwitterionic, non-fouling headgroup.

iii. Copolymers

In one embodiment, the non-fouling material is a copolymer, such as a random copolymer or a block copolymer. Suitable non-zwitterionic monomers include, but are not limited to, the co-monomers discussed above with respect to the undercoating.

D. Tethers and Linkers

As discussed above, the undercoating and/or top coating can be immobilized using a tether or linker. The stability of the undercoating(s) and/or top coating(s) may be dependent on the method of immobilization for each coating on the substrate surface. Variations in tether chemistry can provide an opportunity to develop highly efficient, biocompatible and bioresponsive immobilized non-fouling and/or bioactive agent coatings. The bonding between a tether molecule and the coating and/or a bioactive agent can be covalent, non-covalent, ionic, dispersive, coordinate, chelation type bonding or combinations thereof. To ensure permanent immobilization, a non-labile or un-reactive tether can be synthesized. Such a tether should provide a linkage that is stable in vivo between the substrate surface and the immobilized molecule or material.

Tethers can be formed by synthetic means known in the art including, but not limited to, free radical polymerization, ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET). Tethers can be formed either by grafting from the substrate or by grafting to the substrate and subsequently grafting to the tether the non-fouling material and/or biomolecule.

In one embodiment, the linkers and tethers are responsive to the surrounding environment. For example, the linkers and tethers may release the undercoating and/or top coating under specific conditions, e.g., oxidative conditions, low pH, or when the device arrives at the desired site. Conversely, when the composition is not in the presence of releasing conditions, the linker or tether re-immobilizes the undercoating and/or top coating, which may be present in the surrounding solution or retained within a device in which the coatings are found.

Tethers and linkers may be molecules or polymers containing one or more functional groups including, but not limited to, divinyl compounds, diacrylates, dimethacrylates, diisocyanates, diglycidyl ethers, and dimaleic anhydrides. Alternatively, hetero-bifunctional tethers may be used.

E. Fluorescent and Colormetric Labels

In one embodiment, the surface modification is stained or labeled with one or more colorimetric labels, fluorescence labels, or combinations thereof. These labels are used to visualize the surface modification using the naked eye, spectroscopy, microscopy, or combinations thereof. Suitable microscopy techniques include, but are not limited to, optical microscopy, fluorescent microscopy, and combinations thereof.

The surface can be stained through a chemical reaction or by physical adsorption such as charge-charge interactions, hydrophobic interactions, or hydrophilic interactions. Labeling compounds include, but are not limited to, compounds or derivatives of rhodamine, fluorescein, coumarin, orange B, crystal violets, toluidine blue, methyl violet, nuclear fast red, methylene blue, malachite green, magenta, acriflavine, and other azo compounds.

In another embodiment the surface modification, such as a zwitterionic polymer, is labeled by incorporating one or more reactive labeling monomers into the polymer backbone during polymerization. These labeling monomers include, but not limited to, FITC-methacrylate, FITC-acrylate, rhodamine-methacrylate, rhodamine-acrylate, their derivatives or any other fluorescent acrylate, methacrylate, acrylamide, vinyl compound, diol or diamine. Incorporation of these groups allows for convenient measurement of conformality and/or thickness of the coating. This may be particularly useful as a quality control metric for conformality verification during manufacturing of the coating on an underlying device.

In another embodiment of the surface modification is stained with one or more compounds, which could be easily visualized under an electronic microscope (SEM or TEM). These compounds include, but not limited to osmium tetroxide and ruthenium tetroxide.

F. Bioactive Agents

Therapeutics, diagnostic, and/or prophylactic agents can be immobilized on a substrate. These agents can interact passively or actively with the surrounding in vivo environment. The agents can also be used to alter the surrounding in vivo chemistry or environment. Two or more agents can be immobilized to a substrate surface, wherein the activity of the two agents is greater than either of the agents alone. A substance, material or agent that is not considered active, can become active if an active agent is immobilized on the substance, material or agent. Active agents include, but are not limited to inorganic compounds, organometallic compounds, organic compounds or any synthetic or natural, chemical or biological compounds of known or unknown therapeutic effect.

Cell adhesion agents can be immobilized to the compositions described herein. The efficacy of a cell adhesion agent in binding cells in complex environments may be enhanced by reducing non-specific protein adsorption on the surface from which they are presented, given that cell attachment may be a competitive process with other protein adsorption. Further, there may an advantage to resisting attachment of any cells other than those specifically targeted by the cell adhesion agent to prevent competitive blocking of the surface.

Examples of desirable cell attachment agents include, but are not limited to, integrin binders. Exemplary integrin binders include, but are not limited to, RGD peptides, along with a number of variants that include RGD motifs. Longer variants of this peptide may have more specific target cell binding. Further, the ability to present locally dense concentrations of cell attachment agents may increase the effectiveness of cell attachment by creating multimeric interactions. Other cell adhesion agents include, but are not limited to, REDV peptides. Tailored integrin binders can be used for a variety of applications including osteointegration.

Cell adhesion agents that bind specific immune cells may also benefit from attachment to zwitterions. Adhesion of immune cells to the biomaterial surface activates these cells and prefaces their phenotypic response, such as the transition of monocytes to macrophages that can result, in some cases, in the fusion into undesirable foreign body giant cells. The inherent resistivity to random protein fouling that zwitterions possess provides a unique platform to couple biomolecules that act as specific ligands for immune cells including neutrophils and monocytes. Selection of appropriate ligands may prime these cells for beneficial instead of detrimental functions. These ligands include peptides or proteins that specifically bind immune cell receptors such as integrins, selectins, complement, or Fc gamma. When bound to these cell-associated proteins, such ligands may stimulate intracellular signaling pathways that lead to responses including cytoskeletal rearrangements, production and secretion of molecules including chemokines, cytokines and other chemoattractants, and induction of apoptosis. Desirable behaviors that could be tailored by presentation of biomolecules via zwitterionic tethers may include prevention/reduction in the secretion of proinflammatory cytokines, enhancement of phagocytosis, and modulation of the release of soluble factors that influence tissue-device integration.

Osteointegration may also be promoted or induced by factors which would benefit from the non-fouling properties and stable presentation of non-fouling materials, such as zwitterions. Osteointegration promoting agents include, but are not limited to, bone-morphogenic proteins, such as BMP2 and shortened analogues thereof. Non-fouling surfaces, such as zwitterionic surfaces, may enhance the activity of agents designed to promote desired cell regrowth over a surface. Reducing attachment of neutrophils and macrophages may inhibit the foreign body response and enable desired cell attachment and growth process to be favored.

Presentation of antithrombotic agents may also be more effective when tethered to non-fouling materials, such as zwitterionic materials, relative to other tethers. The process of thrombosis involves both surface and bulk pathways. Zwitterions have shown an ability to reduce platelet attachment and activation, reducing one pathway. Combining an active antithrombotic that assists in the reduction of platelet activation or directly targets additional pathways for thrombosis with a zwitterionic tether could enhance the antithrombotic effect compared to either a non-platelet adherent surface or the antithrombotic agent alone. Suitable antithrombotic agents include, but are not limited to, thrombomodulin, heparin, reversible albumin binders, tissue plasminogen activator binders, transglutimase, reversible NO binders, polylysine, sulphonated polymers, thrombin inhibitors including hirudin, urokinase, and streptokinase.

Device-centered infection remains a large problem. Non-fouling materials, such as zwitterions materials, can by themselves diminish microbial adhesion and retard biofilm development. Prevention of microbial adhesion and biofilm can be further enhanced on non-fouling surfaces, such as zwitterionic surfaces, by presentation of antimicrobials including, but not limited to, membrane-targeting antimicrobial agents, antimicrobial peptides and small molecule antimicrobial agents. Generally, antimicrobial peptides are cationic molecules with spatially separated hydrophobic and charged regions. Exemplary antimicrobial peptides include linear peptides that form an α-helical structure in membranes or peptides that form β-sheet structures, optionally stabilized with disulfide bridges in membranes. Representative antimicrobial peptides include, but are not limited to, cathelicidins, defensins, dermcidin, and more specifically magainin 2, protegrin, protegrin-1, melittin, 11-37, dermaseptin 01, cecropin, caerin, ovispirin, cecropin A melittin hybrid, and alamethicin, or hybrids or analogues of other AmPs. Naturally occurring antimicrobial peptides include peptides from vertebrates and non-vertebrates, including plants, humans, fungi, microbes, and insects.

Antimicrobial peptides can be made from naturally occurring amino acids, non-naturally occurring amino acids (e.g., synthetic or semisynthetic amino acids and peptidomimetics), or combinations thereof. Antimicrobial peptides which retain their activity when immobilized on a surface are generally referred to as membrane-targeting antimicrobial agents. Antimicrobial peptides can be immobilized on the non-fouling coating, the substrate, the undercoat, or combinations thereof by reacting a functional group on the peptide with a functional group on the non-fouling coating, the substrate, and/or the undercoat. For example, the peptide can be designed to have a cysteine residue which can be used to immobilize the peptide on a surface by reacting the thiol group of the cysteine residue with a thiol-reactive group on the surface.

Tethering of these agents via non-fouling materials, such as zwitterions, should provide stable, long-term activity. Additionally, immobilization of enzymes that degrade bacterial attachment and biofilm proteins, such as glycosylases, lyases, and serine-proteases, or those that degrade microbial communication signal molecules, such as N-acyl-homoserine lactone acylases, could provide improved efficacy in prevention of initial microbial adhesion events and subsequent biofilm formation.

Non-fouling surfaces, such as zwitterionic surfaces, may also present a particularly attractive surface for immobilization of biomolecules, such as antibodies, for use as biosensors. Immobilized antibodies on non-fouling surface surfaces, such as zwitterionic surfaces, have been demonstrated to retain both antibody activity and antigen specificity in whole blood. "Smart" implanted medical devices that detect undesirable activation of specific immune pathways, such as proinflammatory cytokines, or the presence of a possible infectious agent, perhaps through detection of a secreted microbial toxin, could be designed, for example, by utilizing specific antibodies or biomolecules tailored to monitor these threats. Appropriate therapeutic strategies could then be employed before an unfavorable outcome, such as infection, arises. The stability of the zwitterionic molecule in vivo provides a unique advantage in this type of scenario due to its longevity.

III. Methods of Making

Non-fouling surfaces, which are substantially more stable in vivo, have been created using graft to chemistries in combination with non-fouling polymeric materials, such as zwitterionic polymers. The coatings created using these grafting methods may be more effective in their ability to retain the desired non-fouling properties over long periods in vivo, even in cases where the coating incurs slight damage (i.e. microscratches). In addition to long-term stability, the monomer and tether chemistries can be tailored in a manner that allows for controlling a coating's response to the surrounding environment as well as controlling coating degradation if desired.

As discussed above, the undercoating(s), top coating, and/or active agent can be immobilized covalently or non-covalently. Methods used to apply covalent coatings include, but are not limited to, dipping, spraying, blade, powder, and painting. Non-covalent methods include, but are not limited to, dipping, spraying, and painting.

Undercoatings can be formed by synthetic means known in the art including, but not limited to, free radical polymerization (e.g., thermal, UV, and/or redox), ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET).

For example, the undercoating can be prepared by polymerizing one or more monomers using polymerization methods known in the art. The substrate can be coated with the undercoat by exposing the surface of the substrate to the undercoating material, for example, by dipping the substrate into a solution of the undercoat. The thickness of the undercoating can be tailored by varying the concentration of undercoat in solution and/or by increasing the number of dip steps and/or the changing the speed of the dip step. A washing step may follow the application of the undercoating before the topcoat is applied.

Optionally, after the dip step, the polymer-coated substrate may be cured to covalently bind the undercoating to the substrate. Following curing, the undercoat-coated substrate is exposed to the topcoat, for example, by dipping the coated substrate into a solution of the topcoat. The substrate may be cured to covalently bind the topcoat to the undercoat.

Functional groups on the substrate which can be used to covalently bind the top coat to the undercoating(s) and/or to a functionalized substrate include, but are not limited to, amines, which can be introduced through aminolysis of the substrate; click chemistry methods wherein the surface for attachment contains azide or terminal alkyne functionality and the coating to be immobilized contains either azide- or terminal alkyne-reactive functionality wherein the surface for attachment does not contain the same functionality as the coating to be immobilized; and immobilization through thiol reactions involving olefins, alpha,beta-unsaturated carbonyls, or other thiols as in the case of disulfide bonding.

Other chemistries can include anionic or cationic reactions, nucleophile-electrophile reactions, addition reactions, such as Michael addition, ring opening methods, such as epoxide or aziridine, and metathesis reactions. Organometallic reactions include chelation type bonding between a mono- or multi-dentate organic ligands and inorganic atoms with empty d-orbitals available for bonding. In some embodiments the chemistries used to immobilize a coating or coating set can be catalyzed or un-catalyzed.

Coatings can be applied by simultaneously dipping the external portion in a polymer solution or dispersion to coat the external portion and flowing a polymer solution or dispersion through the intralumenal portion to coat the intralumenal portion. These unit operations are used commercially to modify marketed short-term antimicrobial catheters. Coating application parameters utilized to effect coating control include the solvent system, percent solids and viscosity, and cure temperature and time. Suitable solvents for the undercoat include, but are not limited to, alcohols, such as methanol or ethanol. Suitable solvents for the topcoat include, but are not limited to, water. Application and cure temperature can vary, for example between ambient and 50° C. so as not to affect physical properties of the underlying polyurethane substrate. Solids content can vary between 0.5-10%, with solution viscosity no higher than 12 cP for ease of handling and application. Typical combined thickness of the under coat and top coat will not exceed 100 μm; however, coating thicknesses greater than 100 μm may be used if desired.

For example, a substrate can be coated with an undercoating by exposing the substrate to a solution of the undercoating. In one embodiment, the substrate is immersed in a solution of the undercoating. The substrate can be dipped once or multiple times. The thickness of the coating can be controlled by the number of dips and/or the rate of immersion. Following dipping, the coated substrates are typically dried to remove solvent. After drying, coated substrates can be heated, for example, 16 hours at 60° C., to cure the undercoating so that it is covalently bound to the substrate.

The top coat can be applied by dipping the undercoat-coated substrate into a solution of top coat. The thickness of the coating can be controlled by the number of dips and/or the rate of immersion. After drying, the top coat can be cured by heating the substrate, for example for 40 hours at 60° C.

As discussed above, many medical device substrates possess internal cavities or lumens which also necessitate coating. All disclosed approaches can be applied both externally and internally to a medical device substrate provided there is open access to the cavity. In one embodiment the internal surface which is coated is the lumen or lumens of a catheter. If internal coating is necessary but cavity access is not available, medical device design may need to be altered to provide at least temporary access tot the cavity for coating.

Bioactive agents can be immobilized onto functionalized substrates, undercoatings, and/or non-fouling materials using the chemistries described above. The chemistries can be modified as the bioactive agent and/or substrate require.

During both the chemistry and the catheter coating optimizations, coated substrates can be characterized for chemical, biological, and mechanical properties to ensure proper alignment with key product requirements. Suitable assays include:

Attenuated Total Reflection IR (ATR-IR) can be utilized to verify the chemical composition of the coating.

Scanning electron microscopy (SEM) can be utilized on the sample cross-section to determine coating thickness. Samples are typically flash frozen in liquid nitrogen and then freeze fractured to prevent any distortion of the coating during sectioning.

Mechanical stability of coatings can be demonstrated by examining both activity and potential cracking (via microscopy) after stretching and bending stresses of the catheter.

An enzyme-linked immunosorbent assay (ELISA) can be used to quantify fibrinogen binding.

Supernatants from samples stored in PBS can be inoculated with bacteria to confirm the lack of any leaching antimicrobial agents that could confound biological testing results A 24-hr biofilm system can be used to assess bacterial growth on coated and control catheter segments using both *S. epidermidis* and *S. aureus*

A 2-hr external flow loop with fresh bovine blood can be used to quantify attachment of radio-labeled platelets as a measure of thrombosis formation Using the assays described above, coating formulations can be optimized to maximize anti-thrombotic, antimicrobial, and anti-adherent properties of catheter substrate materials. For example, for topcoats, the ratio of CBMA to AEMA monomers can be varied from 1:1 to 20:1 to provide maximum protein resistance while still ensuring stable immobilization to the undercoat. NMR analysis (both proton and carbon) can be used to determine the ratio of monomer units incorporated into the polymer. The effect of top coat average molecular weight can be evaluated using dialysis and precipitation of top coat formulations. Effects of molecular weight distribution can be examined using varying free radical initiation schemes including uncontrolled initiation (which typically provide a polydispersity >1.5) and highly controlled initiation through atom transferred radical polymerization (which typically provide a polydispersity <1.1). Gel permeation chromatography (GPC) with refractive index (RI) can be used to measure the molecular weight distribution of all coatings.

IV. Methods of Use

The materials described above may be in the form of a medical device to which the non-fouling material is applied as a coating. Suitable devices include, but are not limited to, surgical, medical or dental instruments, ophthalmic devices, wound treatments (bandages, sutures, cell scaffolds, bone cements, particles), appliances, implants, scaffolding, suturing material, valves, pacemaker, stents, catheters, rods, implants, fracture fixation devices, pumps, tubing, wiring, electrodes, contraceptive devices, feminine hygiene products, endoscopes, wound dressings and other devices, which come into contact with tissue, especially human tissue.

A. Fibrous and Particulate Materials

In one embodiment, the non-fouling materials are coated directly on a fibrous material, incorporated into a fibrous material or coated indirectly on a fibrous material (e.g. coated on a different surface coating). These include wound dressings, bandages, gauze, tape, pads, sponges, including woven and non-woven sponges and those designed specifically for dental or ophthalmic surgeries (See, e.g., U.S. Pat. Nos. 4,098,728; 4,211,227; 4,636,208; 5,180,375; and 6,711,879), paper or polymeric materials used as surgical drapes, disposable diapers, tapes, bandages, feminine products, sutures, and other fibrous materials.

Fibrous materials are also useful in cell culture and tissue engineering devices. Bacterial and fungal contamination is a major problem in eukaryotic cell culture and this provides a safe and effective way to minimize or eliminate contamination of the cultures, while allowing selective attachment of the desired cells through the incorporation of directed adhesion proteins into the material.

The non-fouling agents are also readily bound to particles, including nanoparticles, microparticles, millimeter beads, or formed into micelles, that have uses in a variety of applications including cell culture, as mentioned above, and drug delivery. Non-fouling, biocompatible, polymeric micelles would prevent protein denaturation preventing activation of the immune response allowing for a more stealthy delivery of the desired therapeutic.

B. Implanted and Inserted Materials

The non-fouling material can also be applied directly to, or incorporated in, polymeric, metallic, or ceramic substrates. Suitable devices include, but are not limited to surgical, medical or dental instruments, blood oxygenators, pumps, tubing, wiring, electrodes, contraceptive devices, feminine hygiene products, endoscopes, grafts, stents, pacemakers, implantable cardioverter-defibrillators, cardiac resynchronization therapy devices, ventricular assist devices, heart valves, catheters (including vascular, urinary, neurological, peritoneal, interventional, etc.), shunts, wound drains, dialysis membranes, infusion ports, cochlear implants, endotracheal tubes, guide wires, fluid collection bags, sensors, wound treatments (dressings, bandages, sutures, cell scaffolds, bone cements, particles), ophthalmic devices, orthopedic devices (hip implants, knee implants, spinal implants, screws, plates, rivets, rods, intramedullary nails, bone cements, artificial tendons, and other prosthetics or fracture repair devices), dental implants, breast implants, penile implants, maxillofacial implants, cosmetic implants, valves, appliances, scaffolding, suturing material, needles, hernia repair meshes, tension-free vaginal tape and vaginal slings, tissue regeneration or cell culture devices, or other medical devices used within or in contact with the body or any portion of any of these.

Preferably, the non-fouling coating herein does not significantly adversely affect the desired physical properties of the device including, but not limited to, flexibility, durability, kink resistance, abrasion resistance, thermal and electrical conductivity, tensile strength, hardness, burst pressure, etc. In one embodiment, the tensile strength, modulus, device dimensions, or combinations thereof of the coated substrate are within 20%, preferably within 10%, more preferably within 5%, most preferably within 1% of the tensile strength, modulus, device dimensions, or combinations thereof of the uncoated substrate.

The compositions described herein resist preferably greater than 50%, 55%, 60%, 65%, 70%, 75%, 80%, 85%, 90%, 95%, 99%, or 99.9% of the adsorption of protein from solution, for example phosphate buffered saline (PBS), media, serum, or in vivo relative to an uncoated control for 1 day, 7 days, 14, 21, 30, 45, 60, 90, 120, 180, or 365 days.

C. Non-Medical Applications

The non-fouling materials can also be added to paints and other coatings and filters to prevent mildew, bacterial contamination, and in other applications where it is desirable to prevent fouling, such as marine applications (ship hull coatings), contact lenses, dental implants, coatings for in vivo sensors, textiles such as hospital drapes, gowns, or bedding, ventilation conduits, doorknobs, devices for separations, such as membranes for microbial suspension, biomolecule separation, protein fractionation, cell separation, waste water treatment, water purification, bioreactors, and food processing.

For non-medical applications, the compositions described herein resist preferably greater than 50%, 55%, 60%, 65%, 70%, 75%, 80%, 85%, 90%, 95%, 99%, or 99.9% adsorption of a fouling material relative to an uncoated control for 1 day, 7 days, 14, 21, 30, 45, 60, 90, 120, 180, 365, or 1000 days.

These materials can also be used to treat surfaces of fibers, particulates and films for the applications of textiles, additives, electric/optical appliances, packaging materials and colorants/inks.

The compositions described herein are stable over extended periods of time, retaining at least 25%, 30%, 35%, 40%, 45%, 50%, 55%, 60%, 65%, 70%, 75%, 80%, 85%, 90%, 95%, or 99% of their non-fouling, anti-thrombotic, and/or antimicrobial properties for extended periods of time, for example, at least 1, 7, 14, 21, 30, 45, 60, 90, 120, 180, 365, or 1000 days.

EXAMPLES

Example 1

Preparation of a Coated Substrate

Preparation of an Undercoating

An undercoating, with reactive functional groups for crosslinking, was prepared through free radical polymerization. 2-aminoethyl methacrylate (AEMA, 20-80 mol %), lauryl methacrylate (LMA, 0-50 mol %), 2-hydroxypropyl methacrylate (HPMA, 0-50 mol %) and 3-(trimethoxysilyl) propyl methacrylate (TMOSMA, 0-25 mol %) were mixed in methanol. Azobisisobutyronitrile (AIBN), an initiator, was added and the reaction solution was heated to 60-65° C. The reaction was allowed to proceed for 12-24 hours at 60-65 C, with gentle stirring, under nitrogen. The crude polymer was purified by dialysis against methanol.

Preparation of a Top Coating

A top coating, containing reactive functional groups for crosslinking, was prepared through free radical polymerization. Sulfobetaine methacrylate (SBMA, 25-70 mol %), glycidyl methacrylate methacrylate (GMA, 10-50 mol %), and 2-hydroxypropyl methacrylate (HPMA, 0-50 mol %) were mixed in methanol. Azobisisobutyronitrile (AIBN), an initiator, was added to the reaction solution, which was heated to 60-65° C. The reaction was allowed to proceed for 24 hours at 60-65° C., with gentle stirring, under nitrogen. The crude polymer was purified by dialysis against deionized $H_2O$.

Coating a Substrate Surface with an Undercoating and Top Coating

The purified undercoating polymer was dissolved in methanol. A substrate was dipped into a solution of methanol containing the undercoating polymer. The thickness of the undercoating can be tailored by varying the concentration of the polymer in solution or by increasing the number and speed of each dip step. After this first dipping treatment the coating is cured in an oven (37-80° C.) for 10-24 hours. This heat treatment activates a crosslinking reaction between individual polymer chains, forming covalent bonds between polymer chains stabilizing the undercoating on the substrate surface. The resulting polymer-treated substrate is then dipped in an aqueous solution containing purified top coating polymer. The coating was cured in an oven at 37-80° C. for 12-48 hours. After curing, the top coating polymer is covalently bound on the undercoating and the substrate is coated with a complete non-fouling coating set.

Example 2

Synthesis of an Undercoating

A nitrogen purged solution of 3.4 g laurylmethacrylate, 4.25 g hydroxypropylmethacrylate, 1.56 g trimethoxysilylpropylmethacrylate, 1.20 g aminoethylmethacrylamide hydrochloride salt, and 0.40 g azoisobutyronitrile in 90 mL anhydrous methanol was heated (64° C.) 14 h. After allowing the mixture to cool to room temperature, the solution was dialyzed against anhydrous methanol using benzylated dialysis tubing to afford a solution of undercoating in methanol.

Example 3

Synthesis of a Top Coat

A nitrogen purged solution of 1.08 g glycidylmethacrylate, 4.2 g N-(3-sulfopropyl)-N-methacryloxyethyl-N,N-dimethylammonium betaine, 0.24 g azoisobutyronitrile in 90 mL anhydrous methanol was heated (64° C.) 14 h. After allowing the solution to cool to room temperature, the solution was decanted from the precipitate. The precipitate was washed twice with anhydrous methanol and dried under vacuum. This topcoat is referred to as the H topcoat.

Example 4

Top Coating Synthesis by Controlled Radical Polymerization

Copper (1) bromide was added to a flask (125 mL) containing a stir bar. The flask was sealed with a septum and the flask was flushed with argon for 30 minutes. Inhibitor was removed from glycidyl methacrylate (GMA) using an inhibitor removal column. Inhibitor free GMA (0.7 g) was diluted with 6.3 mL of methanol. This solution was placed in a separate flask, which was sealed with a septum. 3-Bromo-2-butanone (0.35 g) and methanol (0.90 mL) were added to a separate flask. Bipyridine (0.4 g) was dissolved in methanol (8 mL), in a separate flask, which was sealed with a septum. A 10% solution of N-(3-sulfopropyl)-N-methacryloxyethyl-N,N-dimethylammonium betaine (SBMA) was prepared in 25 mL of a 75:25 mixture of methanol: water. Argon was bubbled through all of the solutions for 1 hour.

After one hour, bipyridine (1 mL) was added, by syringe, to the flask containing the copper (I) bromide, followed by the addition of the GMA solution (1.75 mL). To initiate the reaction, 3-bromo-2-butanone (0.046 mL) was added, by syringe, to the reaction mixture containing the copper (I) bromide, GMA, and bipyridine. This reaction was allowed to proceed for 1 hour at room temperature, with vigorous stirring. Following the initial reaction, SBMA (45 mL) was added to the reaction flask. This reaction was allowed to proceed for 8 hours, before the reaction flask was opened to the air. Any remaining solution was decanted from the precipitate that had formed. The precipitate was then dissolved in water, centrifuged, and the solution was decanted and reserved. The reserved solution was dried by lyophilization.

In another example both the GMA and SBMA monomers were added to the reaction flask at the same time.

Example 5

Coating Polyurethane Rods

Step 1. Preparing test articles. CARBOTHANE® (20% barium sulfate) rod extrusion (OD 0.118±0.002) was cut into 15 cm long test articles. The test articles were soaked in heptane for 5 minutes and then dried on aluminum foil for 1 hour at room temperature (RT).

Step 2. Dipping process in undercoating. The undercoating made in Example 2 was put into a cylindrical glass and held with clamps below an actuator that allowed the test articles to be lowered into and lifted out of the undercoating solution. The test articles were hung from the actuator with alligator clamps and lowered at a rate of ~0.013 m/s. Once the test articles were completely immersed in the undercoating solution (5%) they were immediate lifted out of the solution at a rate of 0.012 m/s. Once dipped, all test articles were hung with alligator clamps from a rack to dry at room temperature for 30 minutes.

Step 3. Undercoating curing process. After drying, all test articles were transferred and hung in an oven for 16 hours at 60° C. to dry. The test articles were then removed from the oven and cooled to room temperature before dipping in the H-topcoat solution.

Step 4. Dipping process in H-topcoat. A solution (5%) of top coat made in Example 3 was prepared. The H-topcoat solution was put into a cylindrical glass and held with clamps below an actuator that allowed the test articles to be lowered into and lifted out of the H-topcoat solution. The test articles were hung from the actuator with alligator clamps and lowered at a rate of ~0.013 m/s. Once the test articles were completely immersed in the topcoat solution they were immediate lifted out of the solution at a rate of 0.012 m/s. Once dipped, all test articles were hung with alligator clamps from a rack to dry at room temperature for 30 minutes.

Step 3. H-topcoat curing process. After drying, all test articles were transferred and hung in an oven for 40 hours at 60° C. The test articles were then removed from the oven and cooled to room temperature (RT).

Example 6

Antimicrobial Activity

A model for biofilm formation of S. epidermidis ATCC 35984 using a CDC biofilm reactor system has been developed. Briefly, the system consists of a stirred glass reactor vessel with inlet and outlet ports for sterile media addition and removal, as well as a sample holder for our materials. The culture conditions (media formulation and media flow rate) were modified slightly from those described in the current ASTM method (ASTM E2562-07) to allow robust surface growth of S. epidermidis on our control PU materials, while minimizing planktonic bacterial growth. Materials were seeded with bacteria for 2 hrs (planktonic concentration ~$1 \times 10^6$ CFU/ml in PBS with agitation at 37° C.), placed in the reactor system, and incubated for 24 his at 37° C. with a continual exchange of sterile media. After 24 hrs, accumulated biofilm on materials were removed by sonication and enumerated on TSA (tryptic soy agar) plates. Undercoat-topcoat formulations described in Example 5 above have achieved 99% reduction in colonization in this assay relative to uncoated polyurethane.

Example 7

Antimicrobial Activity after Serum Exposure

Antimicrobial activity of the samples produced in Example 5 was measure using by using a colonization assay pre-incubation with 50% fetal bovine serum for 18-20 hours at 120 RPM at 37° C., which is preferred. Following pre-incubation, samples are placed in Staphylococcus aureus (S. aureus, ATCC 25923) which has been diluted from an overnight culture to a planktonic concentration of $1-3 \times 10^5$ CFU/mL in 1% tryptone soy broth (TSB). Samples are incubated with bacteria for 24-26 hrs with agitation (120 rpm) at 37° C. The concentration of TSB varies with the organism being used. After incubation, the samples are placed in 3 ml PBS for 5 min at 240 RPM at 37° C. to remove bacteria not tightly attached. Then accumulated bacteria on materials are removed by sonication in a new solution of PBS and the total number of bacterial cells quantified through dilution plating. A log reduction of 1.16 relative to uncoated CARBOTHANE® was achieved.

We claim:

1. A composition comprising a functionalized substrate in the form of a medical device containing lumens, cavities, porous structures, or combinations thereof, the functionalized substrate having a polymeric undercoat immobilized thereon and a non-fouling polymeric topcoat copolymer covalently bound to the polymeric undercoat, the polymeric undercoat being between the functionalized substrate and the non-fouling polymeric topcoat copolymer, wherein more than 35 mole % of the polymerized monomers comprised by the non-fouling polymeric topcoat copolymer are polyether moieties or phosphorylcholine, sulfobetaine or carboxybetaine zwitterionic moieties, the polymeric undercoat and the non-fouling polymeric topcoat copolymer comprising complementary reactive functional groups wherein the non-fouling polymeric topcoat copolymer is covalently bound to the polymeric undercoat via covalent bonds formed by the complementary reactive functional groups.

2. The composition of claim 1, wherein the substrate comprises a polymer and the polymer is selected from the group consisting of polystyrene and substituted polystyrenes, poly(urethane)s, polyacrylates and polymethacrylates, polyacrylamides and polymethacrylamides, polyesters, polysiloxanes, polyethers, poly(orthoester), poly(carbonates), poly(hydroxyalkanoate)s, polyfluorocarbons, silicones, epoxy resins, polyamides and copolymers thereof, nylon, polyalkenes, phenolic resins, natural and synthetic elastomers, adhesives and sealants, polyolefins, polysulfones, polyacrylonitrile, polysaccharides, and combinations thereof.

3. The composition of claim 2, wherein the polymer is polyurethane or polycarbonate-based polyurethanes.

4. The composition of claim 2 wherein the complementary reactive functional groups are epoxy-amine, isocyanate-carboxyl, glycidyl-anhydride, amine-anhydride, silanol-silanol, isocyanate-amine, carboxyl-amine, or hydroxyl-carboxyl.

5. The composition of claim 1, wherein the complementary reactive functional groups are epoxy-amine, isocyanate-carboxyl, glycidyl-anhydride, amine-anhydride, silanol-silanol, isocyanate-amine, carboxyl-amine, or hydroxyl-carboxyl.

6. The composition of claim 5, wherein the polymeric undercoat comprises a homopolymer or copolymer formed by condensation or radical polymerization of one or more monomers selected from the group consisting of acrylates, acrylamides, vinyl compounds, di, tri-, and tetra-isocyanates, alcohols, amines, thiocyanates, lactones, lactams, and combinations thereof.

7. The composition of claim 6, wherein the polymeric undercoat comprises a homopolymer or copolymer formed by condensation or radical polymerization of one or more acrylate monomers.

8. The composition of claim 7, wherein the polymeric undercoat comprises a copolymer of glycidyl methacrylate (GMA), 2-hydroxypropyl methacrylate (HPMA), lauryl methacrylate (LMA), and trimethoxysilyl methacrylate (TMOSMA).

9. The composition of claim 1, wherein more than 35 mole % of the polymerized monomers comprised by the non-fouling polymeric topcoat copolymer are phosphorylcholine, sulfobetaine or carboxybetaine zwitterionic moieties.

10. The composition of claim 1, wherein the non-fouling polymeric topcoat copolymer further comprises one or more polymerized monomers selected from the group consisting of acrylates, acrylamides, vinyl compounds, di, tri-, and tetra-isocyanates, alcohols, amines, thiocyanates, lactones, lactams, and combinations thereof.

11. The composition of claim 10, wherein the non-fouling polymeric topcoat copolymer comprises 25-70 mol % sulfobetaine methacrylate, 10-50 mol % glycidyl methacrylate methacrylate, and 0-50 mol % 2-hydroxypropyl methacrylate.

12. The composition of claim 1, wherein the non-fouling polymeric topcoat copolymer is grafted to the polymeric undercoat through a tether.

13. The composition of claim 12, wherein the tether is part of the non-fouling polymeric topcoat copolymer.

14. The composition of claim 12, wherein the tether is a moiety immobilized on the polymeric undercoat.

15. The composition of claim 1, wherein the non-fouling polymeric topcoat copolymer is in the form of a brush or a comb.

16. The composition of claim 1, wherein the non-fouling polymeric topcoat copolymer, the polymeric undercoat, the functionalized substrate, or combinations thereof have immobilized thereon one or more bioactive agents.

17. The composition of claim 13, wherein the one or more bioactive agents are immobilized covalently or non-covalently on the non-fouling topcoat copolymer, the polymeric undercoat, the functionalized substrate, or combinations thereof.

18. The composition of claim 17, wherein the one or more bioactive agents are immobilized to the non-fouling topcoat copolymer, the polymeric undercoat, the functionalized substrate, or combinations thereof, through a tether.

19. The composition of claim 1, wherein the composition reduces fouling by greater than 80% after storage in phosphate buffered saline (PBS) containing protein, media, or serum at 37° C. for a period of at least 7 days compared to uncoated substrate.

20. The composition of claim 1, wherein the composition is biocompatible.

21. The composition of claim 1, wherein the composition is antimicrobial.

22. The composition of claim 1, wherein the composition is anti-thrombogenic.

23. The composition of claim 1 wherein the composition retains greater than 80% of its original anti-thrombogenic activity, in PBS containing serum for a time of 30 days.

24. The composition of claim 1, wherein the medical device is a vascularly inserted catheter selected from the group consisting of a peripherally inserted central catheter (PICC), central venous catheter (CVC), and hemodialysis catheter.

25. The composition of claim 1, wherein the tensile strength, modulus, device dimensions, or combinations thereof are within 20% of the tensile strength, modulus, device dimensions, or combinations thereof of the uncoated substrate.

26. A method of making a composition in the form of a medical device containing lumens, cavities, porous structures, or combinations thereof, the method comprising immobilizing a polymeric undercoat having reactive functional groups on the medical device and grafting a non-fouling polymeric topcoat copolymer to the immobilized polymeric undercoat, the non-fouling polymeric topcoat copolymer having reactive functional groups, the undercoat reactive functional groups and the non-fouling polymeric topcoat copolymer reactive functional groups being complementary wherein the non-fouling polymeric topcoat copolymer is covalently bound to the polymeric undercoat via covalent bond formation between the complementary reactive functional groups and more than 35 mole % of the polymerized monomers comprised by the non-fouling polymeric topcoat copolymer are polyether moieties or phosphorylcholine, sulfobetaine or carboxybetaine zwitterionic moieties.

27. The method of claim 26, wherein the non-fouling polymeric topcoat copolymer is grafted to the immobilized undercoat using one or more polymerized monomers having unsaturated bonds.

28. The method of claim 26 wherein the medical device is a vascularly inserted catheter selected from the group consisting of a peripherally inserted central catheter (PICC), central venous catheter (CVC), and hemodialysis catheter.

29. The method of claim 26 wherein the substrate comprises a polymer and the polymer is selected from the group consisting of polystyrene and substituted polystyrenes, poly(urethane)s, polyacrylates and polymethacrylates, polyacrylamides and polymethacrylamides, polyesters, polysiloxanes, polyethers, poly(orthoester), poly(carbonates), poly(hydroxyalkanoate)s, polyfluorocarbons, silicones, epoxy resins, polyamides and copolymers thereof, nylon, polyalkenes, phenolic resins, natural and synthetic elastomers, adhesives and sealants, polyolefins, polysulfones, polyacrylonitrile, polysaccharides, and combinations thereof.

30. The method of claim 26 wherein the substrate comprises a polymer and the polymer is polyurethane or a polycarbonate-based polyurethane.

31. The method of claim 26 wherein the complementary reactive functional groups are epoxy-amine, isocyanate-carboxyl, glycidyl-anhydride, amine-anhydride, silanol-silanol, isocyanate-amine, carboxyl-amine, or hydroxyl-carboxyl.

32. The method of claim 26 wherein the polymeric undercoat comprises a homopolymer or copolymer formed by condensation or radical polymerization of one or more acrylate monomers.

33. The method of claim 26 wherein the non-fouling polymeric topcoat copolymer is a random copolymer or a block copolymer.

34. The method of claim 26 wherein more than 35 mole % of the polymerized monomers comprised by the non-fouling polymeric topcoat copolymer are polyether moieties.

35. The method of claim 26 wherein more than 35 mole % of the polymerized monomers comprised by the non-fouling polymeric topcoat copolymer are a phosphorylcholine, sulfobetaine, or carboxybetaine zwitterionic moiety.

36. The method of claim 26 wherein more than 35 mole % of the polymerized monomers comprised by the non-fouling polymeric topcoat copolymer are a sulfobetaine or carboxybetaine zwitterionic moiety.

37. The composition of claim 1 wherein more than 35 mole % of the polymerized monomers comprised by the non-fouling polymeric topcoat copolymer are a phosphorylcholine, sulfobetaine, or carboxybetaine zwitterionic moiety.

38. The composition of claim 37 wherein more than 35 mole % of the polymerized monomers comprised by the non-fouling polymeric topcoat copolymer are a sulfobetaine or carboxybetaine zwitterionic moiety.

* * * * *